(12) United States Patent
Zhou et al.

(10) Patent No.: US 10,220,064 B2
(45) Date of Patent: Mar. 5, 2019

(54) **CARBOHYDRATE COMPOSITION EXTRACTED FROM *PANAX GINSENG* AND ITS USE IN THE TREATMENT OF ISCHEMIC CONDITIONS**

(71) Applicant: Macau University of Science and Technology, Taipa (MO)

(72) Inventors: Hua Zhou, Taipa (MO); Quanbing Han, Taipa (MO); Yihan Zuo, Taipa (MO); Liang Liu, Taipa (MO); Ruiqi Yue, Taipa (MO)

(73) Assignee: MACAU UNIVERSITY OF SCIENCE AND TECHNOLOGY, Taipa (MO)

( * ) Notice: Subject to any disclaimer, the term of this patent is extended or adjusted under 35 U.S.C. 154(b) by 0 days.

(21) Appl. No.: 15/345,842

(22) Filed: Nov. 8, 2016

(65) Prior Publication Data

US 2018/0125906 A1    May 10, 2018

(51) Int. Cl.
*A61K 36/258*  (2006.01)
*A61K 31/715*  (2006.01)

(52) U.S. Cl.
CPC .......... *A61K 36/258* (2013.01); *A61K 31/715* (2013.01)

(58) Field of Classification Search
CPC ........................... A61K 36/258; A61K 31/715
See application file for complete search history.

(56) References Cited

FOREIGN PATENT DOCUMENTS

CN        1899400 A1 *  1/2007  ........... A61K 36/714

OTHER PUBLICATIONS

EPO machine translation of CN 1899400 A1, https://worldwide.espacenet.com, accessed online on Jan. 17, 2018. (Year: 2018).*
Dong, G., et al. Rg1 prevents myocardial hypoxia/reoxygenation injury by regulating mitochondrial dynamics imbalance via modulation of glutamate dehydrogenase and mitofusin 2. Mitochondrion 26, 7-18 (2016).
Zheng, S.-d., Wu, H.-j. & Wu, D.-I. Roles and mechanisms of ginseng in protecting heart. Chinese journal of integrative medicine 18, 548-555 (2012).
Zhou, H., et al. Ginseng protects rodent hearts from acute myocardial ischemia—reperfusion injury through GR/ER-activated RISK pathway in an endothelial NOS-dependent mechanism. J Ethnopharmacol 135, 287-298 (2011).
Xu, J., et al. A novel and rapid HPGPC-based strategy for quality control of saccharide-dominant herbal materials: Dendrobium officinale, a case study. Anal Bioanal Chem 406, 6409-6417 (2014).
Dubois, M., Gilles, K.A., Hamilton, J.K., Rebers, P.A. & Smith, F. Colorimetric method for determination of sugars and related substances. Analytical chemistry 28, 350-356 (1956).
Blumenkrantz, N. & Asboe-Hansen, G. New method for quantitative determination of uronic acids. Anal Biochem 54, 484-489 (1973).
Chiu, P.Y., Chen, N., Leong, P.K., Leung, H.Y. & Ko, K.M. Schisandrin B elicits a glutathione antioxidant response and protects against apoptosis via the redox-sensitive ERK/Nrf2 pathway in H9c2 cells. Molecular and cellular biochemistry 350, 237-250 (2011).
Aguilar, D.C., Strom, J., Xu, B., Kappeler, K. & Chen, Q.M. Expression of glucocorticoid induced leucine zipper (GILZ) in cardiomyocytes. Cardiovasc Toxicol 13, 91-99 (2013).
Guo, R., et al. Exogenous hydrogen sulfide protects against doxorubicin-induced inflammation and cytotoxicity by inhibiting p38MAPK/NFκB pathway in H9c2 cardiac cells. Cellular Physiology and Biochemistry 32, 1668-1680 (2013).
Wei, C.D., et al. Globular adiponectin protects H9c2 cells from palmitate-induced apoptosis via Akt and ERK1/2 signaling pathways. Lipids Health Dis 11, 135 (2012).
Diffley, J.M., et al. Apoptosis induction by oxidized glycated LDL in human retinal capillary pericytes is independent of activation of MAPK signaling pathways. Molecular Vision 15, 135-145 (2009).
Park, E.S., et al. Cardioprotective effects of rhamnetin in H9c2 cardiomyoblast cells under H2O2-induced apoptosis. J Ethnopharmacol 153, 552-560 (2014).
Sathishkumar, K., et al. Determination of glutathione, mitochondrial transmembrane potential, and cytotoxicity in H9c2 cardiomyoblasts exposed to reactive oxygen and nitrogen species. Free Radicals and Antioxidant Protocols, 51-61 (2010).
Chen, X.P., et al. SOD1 aggregation in astrocytes following ischemia/reperfusion injury: a role of NO-mediated S-nitrosylation of protein disulfide isomerase (PDI). Journal of Neuroinflammation 9(2012).
Lu, C., et al. Scavenger receptor class-A has a central role in cerebral ischemia-reperfusion injury. J Cerebr Blood F Met 30, 1972-1981 (2010).
Duicu, O.M., et al. Assessment of the Effects of Methylene Blue on Cellular Bioenergetics in H9c2 Cells. Rev Chim-Bucharest 66, 519-522 (2015).

(Continued)

*Primary Examiner* — Jonathan S Lau
(74) *Attorney, Agent, or Firm* — Renner Kenner Greive Bobak Taylor & Weber

(57) ABSTRACT

Methods of treating a subject suffering from an ischemic condition and of preventing an ischemia-reperfusion injury in a subject suffering from an ischemic condition, particularly, but not exclusively ischemic heart disease and the subject is in particular a human, includes administering an effective amount of a carbohydrate composition extracted from *Panax ginseng* to the subject. The carbohydrate composition of the present invention extracted from *Panax ginseng* shows exceptional cardio-protective effect and, thus, provides a highly advantageous and highly promising treatment option for treatment of ischemic conditions and prevention of ischemia-reperfusion injury. The present invention further provides a method of protecting cells against hypoxia and reoxygenation induced cell death. Still further, the present invention provides a carbohydrate composition extracted from *Panax ginseng* and a pharmaceutical formulation comprising it.

18 Claims, 36 Drawing Sheets

(56) References Cited

OTHER PUBLICATIONS

Sardao, V.A., Oliveira, P.J., Holy, J., Oliveira, C.R. & Wallace, K.B. Morphological alterations induced by doxorubicin on H9c2 myoblasts: nuclear, mitochondrial, and cytoskeletal targets. Cell Biol Toxicol 25, 227-243 (2009).

Janjua, M.B., et al. Cardioprotective Benefits of Adenosine Triphosphate: Sensitive Potassium Channel Opener Diazoxide Are Lost with Administration after the Onset of Stress in Mouse and Human Myocytes. Journal of the American College of Surgeons 219, 803-813 (2014).

Henn, M.C., et al. Diazoxide Cardioprotection Is Independent of Adenosine Triphosphate-Sensitive Potassium Channel Kir6.1 Subunit in Response to Stress. Journal of the American College of Surgeons 221, 319-325 (2015).

\* cited by examiner

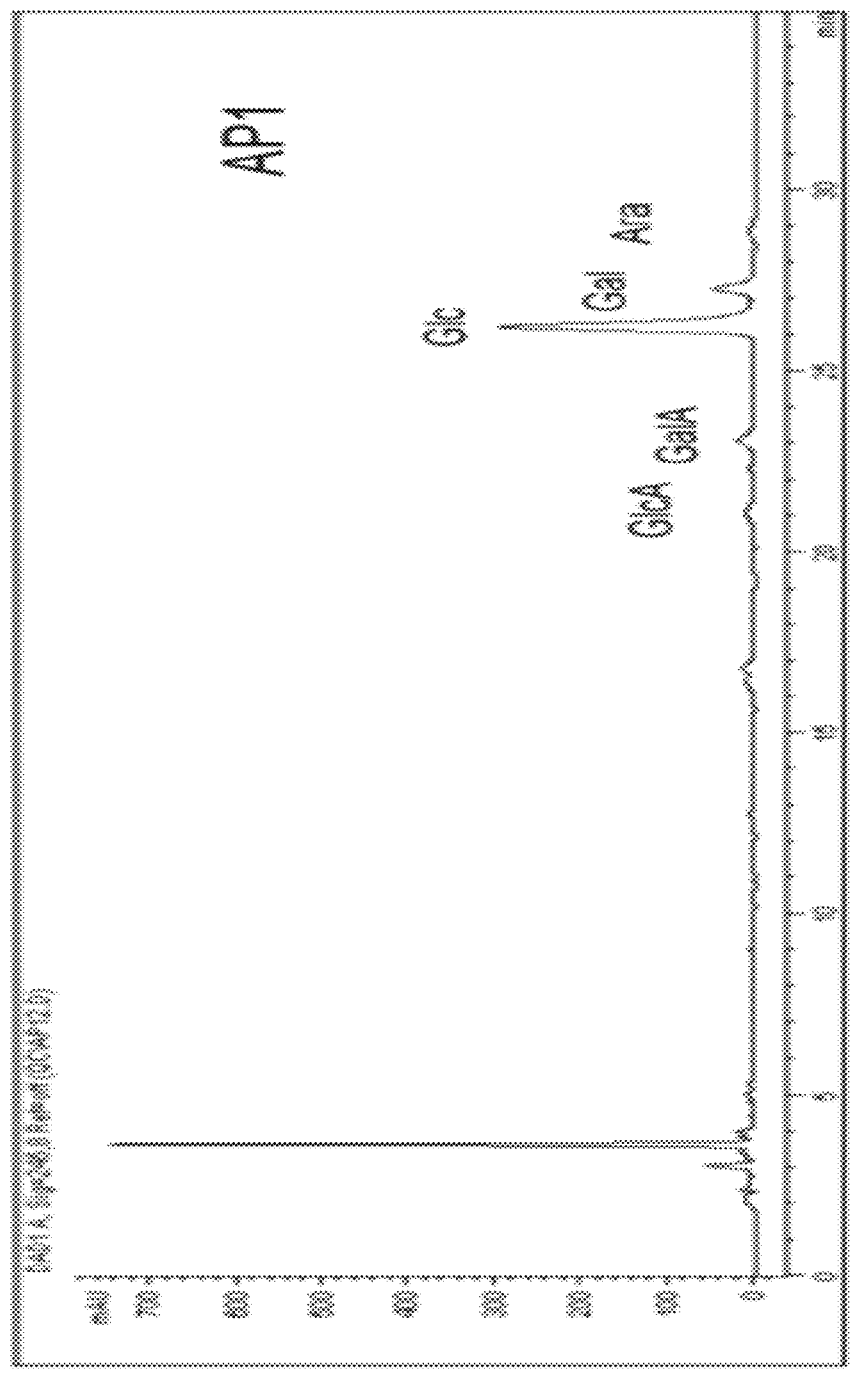

CARBOHYDRATE COMPOSITION EXTRACTED FROM *PANAX GINSENG* AND ITS USE IN THE TREATMENT OF ISCHEMIC CONDITIONS

TECHNICAL FIELD

The present invention relates to methods of treating a subject suffering from an ischemic condition and of preventing an ischemia-reperfusion injury in a subject suffering from an ischemic condition. The ischemic condition is especially but not exclusively ischemic heart disease and the subject is a human. The methods comprise administering an effective amount of a carbohydrate composition extracted from *Panax ginseng* to the subject. The carbohydrate composition in particular comprises at least one polysaccharide which is an acidic heteroglycan. The present invention further provides a method of protecting cells against hypoxia and reoxygenation induced cell death, a carbohydrate composition extracted from *Panax ginseng* and the method for its preparation and a pharmaceutical formulation comprising it.

BACKGROUND OF THE INVENTION

Ischemic conditions, in particular ischemic heart disease (IHD), represent a leading cause of human death. Data issued by the World Health Organization (WHO) in 2014 indicate that about 7.4 million people died due to ischemic heart disease in 2012 which makes IHD to the no. 1 in the list of life-threatening conditions. At present, the approach for curing IHD is to re-perfuse the affected area through Coronary Artery Bypass Grafting (GABG) or Percutaneous Coronary Interventions (PCI). However, if reperfusion is delayed, this may exacerbate the myocardial injury known as ischemia-reperfusion (I/R) injury.

Available medical therapies such as calcium channel blockers most often fail to provide sufficient therapeutic efficacy and may even enhance the risk of heart attacks. Further, the mechanisms of IHD are quite complex. How to increase the effectiveness of the treatment is, thus, of significant importance. Accordingly, there remains a strong need for further treatment options in treating ischemic conditions like IHD in particular for those which are able to protect against hypoxia and reoxygenation induced cell death.

Recently, Traditional Chinese medicine as well as complementary and alternative medicine has getting popular. Traditional Chinese medicines based on plant materials as well as respective components gained from plants usually allow for treatment of various diseases and conditions while bearing a reduced risk for side effects. In view of the rich medicinal plant resources, respective medicines can usually be produced in a cost-effective way. Accordingly, there has been a lot of research with regard to plants and respective ingredients for treatment of several conditions.

Traditional Chinese medicine is usually characterized by multiple components targeting multiple pathways at multiple levels to produce synergistic effects and, thus, might be a valuable treatment option for IHD, too. For example, *Panax ginseng* C. A. Meyer (*ginseng*) has been used as a classic traditional Chinese medicine quite for a long time, wherein the whole *ginseng* extract was assumed to have cardio-protective effects (Zheng, S.-D. et al., Chinese journal of integrative medicine 18, 548-555, 2012). However, it seems that ginsenosides might only partially contribute to said effects (Zhou, H. et al., J Ethnopharmacol 135, 287-298, 2011).

Since diversified components in Chinese herbal medicines often act via multiple modes, there is a strong need for identifying and providing components in a rather isolated form with sufficient therapeutic efficiency, in particular suitable for treatment of ischemic conditions. Having those active ingredients could further reduce the risk of side effects or interactions which might limit the therapeutic use due to the presence of further ingredients with reduced or insufficient efficacy for treating the respective disease.

SUMMARY OF THE INVENTION

The first aspect of the present invention relates to a method of treating a subject suffering from an ischemic condition and a method of preventing an ischemia-reperfusion injury in a subject suffering from an ischemic condition, which ischemic condition is in particular ischemic heart disease.

Said methods comprise administering an effective amount of a carbohydrate composition extracted from *Panax ginseng* to the subject, in particular a human.

The carbohydrate composition extracted from *Panax ginseng* comprises a carbohydrate portion, preferably formed by at least one polysaccharide, with an amount of more than 50% by weight based on the weight of the carbohydrate composition. In particular embodiments of the present invention, the carbohydrate portion comprises and in particular essentially consists of at least one polysaccharide which is an acidic heteroglycan. Further preferably, the carbohydrate composition comprises at least 85% by weight of the polysaccharide based on the weight of the carbohydrate composition. In particular, glucose and galactose are the main monosaccharides forming the at least one polysaccharide.

The carbohydrate composition is in particular extracted from *Panax ginseng* with an extraction comprising steps of:

(i) providing a crude *Panax ginseng* extract comprising contacting *Panax ginseng* plant material with an extraction solvent comprising an aliphatic alcohol; and (ii) isolating the carbohydrate composition from the crude *Panax ginseng* extract of step (i).

The crude *Panax ginseng* extract obtained in step (i) is in particular a standardized *Panax ginseng* extract, i.e. is standardized to contain a predetermined amount of ginsenosides, most preferably Rg1, Re, Rb1, Rc, Rb2 and Rd with amounts of about 8.08 mg/g, about 7.64 mg/g, about 11.58 mg/g, about 10.35 mg/g, about 6.67 mg/g and about 4.50 mg/g, respectively.

Step (ii) in particular comprises steps of:

a) optionally fractionating the crude *Panax ginseng* extract for obtaining a carbohydrate-enriched *Panax ginseng* extract in particular comprising subjecting the crude *Panax ginseng* extract to a fluid-fluid chromatography preferably carried out as a high-speed counter-current chromatography (HSCCC);

b) adding water and an aliphatic alcohol, in particular ethanol, to the crude *Panax ginseng* extract of step (i) or to the carbohydrate-enriched *Panax ginseng* extract of step a) for obtaining a carbohydrate-enriched precipitate;

c) subjecting the carbohydrate-enriched precipitate to an anion-exchange chromatography with an eluting solvent, in particular comprising water and sodium chloride, for obtaining an eluate comprising the carbohydrate composition;

d) concentrating the eluate of step c) for obtaining the carbohydrate composition in particular including freeze-drying.

In another aspect, the present invention provides a method of protecting cells against hypoxia and reoxygenation (H/R) induced cell death. The method comprises contacting the cells with a carbohydrate composition extracted from *Panax ginseng*, in particular with between 6.25 µg/ml and 800 µg/ml of the carbohydrate composition for at least 24 h. The cells are in particular cardiomyocytes, i.e. from the cardiac muscle.

Further provided is a method for preparing a carbohydrate composition by extracting the carbohydrate composition from *Panax ginseng* as described above.

The present invention further refers to the carbohydrate composition extracted from *Panax ginseng*, in particular comprising at least one polysaccharide which is an acidic heteroglycan.

The present invention further provides a pharmaceutical formulation comprising an effective amount of the carbohydrate composition described above and at least one pharmaceutically acceptable excipient such as selected from a diluent, a filler, a binder, a disintegrant, a lubricant, a coloring agent, a surfactant or a preservative.

The invention is also the carbohydrate composition described above for use as a medicament for the treatment of an ischemic condition and/or for preventing an ischemia-reperfusion injury in a subject suffering from an ischemic condition, in particular ischemic heart disease. Another aspect of the invention refers to the use of the carbohydrate composition described above for preparing a medicament for treatment of an ischemic condition and/or for preventing an ischemia-reperfusion injury in a subject suffering from an ischemic condition, in particular ischemic heart disease. The present invention also relates to the use of the carbohydrate composition as described above for protecting cells against hypoxia and reoxygenation induced cell death.

The carbohydrate composition extracted from *Panax ginseng* proved to exceptionally increase cell viability and reduce apoptosis rate under hypoxia and reoxygenation conditions. In particular, the carbohydrate composition extracted from *Panax ginseng* according to the present invention proved to prevent morphological changes of cells, to protect the mitochondrial function such as by increasing the mitochondrial membrane potential, to increase the ATP level, to increase the Bcl-2/Bax ratio and to activate the pro-survival Reperfusion Injury Salvage Kinase (RISK) Pathway.

In particular, a carbohydrate composition extracted from *Panax ginseng* comprising an acidic heteroglycan with a carbohydrate content of about 90.28% by weight comprising glucose with about 76.31% by weight, galactose about 12.70% by weight, galacturonic acid about 5.64% by weight, arabinose about 3.72% by weight, and glucuronic acid about 1.64% by weight and with a total protein content of about 9.85% by weight and an apparent molecular weight of about $3.8 \times 10^4$ Da demonstrated an exceptionally high potency in protecting cardiomyocytes against hypoxia and reoxygenation induced cell death. The experiments confirmed that said carbohydrate composition in particular increased the protein level of the steroid hormone receptors GR and ER and the phosphorylated expression of PI3K/Akt, Erk1/2 and eNOS, and NO production in a dose dependent manner. The inventors assume that it protects cardiomyocytes from H/R induced cell apoptosis by increasing the ratio of Bcl2/Bax and by inhibiting the activities of caspase-3/7 and -9. It significantly stimulated cellular energy metabolisms and proved to suppress H/R induced loss of mitochondrial membrane potential in the cardiomyocytes, too.

The results confirm for the first time that a carbohydrate composition extracted from *Panax ginseng* has an exceptional cardio-protective effect which is expected to follow from the regulation of the mitochondrial metabolism and RISK pathway, in particular its cardio-protective potential exceeds the cardio-protective potential of the crude or total *Panax ginseng* extract. In other words, the inventors unexpectedly found that a total *ginseng* extract is less potent than the carbohydrate composition, in particular polysaccharides, obtainable from said total extract. The carbohydrate composition extracted from *Panax ginseng*, thus, provides a highly advantageous and highly promising treatment option for cardio-protection and treatment of IHD.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 1A shows the TLC spectrum of fractions 1 to 17 of RSE. FIG. 1B shows the TLC spectrum of fractions 18 to 34 of RSE. FIG. 1C shows the TLC spectrum of fractions 35 to 51 of RSE.

FIGS. 6A and 6B show the components of carbohydrate compositions of the present invention referenced as NP and AP1 as revealed by HPLC. HPLC analysis of 1-Phenyl-3-methyl-5-pyrazolone (PMP) derivatives of monosaccharides was performed on Agilent 1100 system with a diode array detector, and samples were loaded on an Alltech XDB-C18 column (250 mm×4.6 mm i.d., 5 μm) and eluted with phase A: 100 mM ammonium acetate aqueous solution (pH 5.58) and phase B: acetonitrile (0~5 min, 17~20% B; 5~30 min, 20~28% B) at 1 ml/min. UV detection wavelength was set at 245 nm. FIG. 6A refers to NP and FIG. 6B refers to AP1.

FIG. 8A shows H9c2 normal cells. FIG. 8B shows H9c2 cells exposed to hypoxia for 3 h followed by reoxygenation for 4 h. FIG. 8C shows H9c2 cells pretreated with 200 μg/mL of AP1 for 1 h and then exposed to hypoxia for 3 h followed by reoxygenation for 4 h. FIG. 8D shows H9c2 cells pretreated with 200 μg/mL of RSE for 1 h and then exposed to hypoxia for 3 h followed by reoxygenation for 4 h. FIG. 8E shows H9c2 cells pretreated with 100 μM of diazoxide (DZ) for 1 h and then exposed to hypoxia for 3 h followed by reoxygenation for 4 h. All photos (magnification power 200×) were taken after reoxygenation.

FIG. 10A shows the effects of AP1 treatment on the expression of GR with Western blotting analysis. FIG. 10B shows the effects of AP1 treatment on the expression of ER with Western blotting analysis. FIG. 10C shows the effects of AP1 treatment on activation and expression of Erk1/2 with Western blotting analysis. FIG. 10D shows the effects of AP1 treatment on activation and expression of P38 with Western blotting analysis. FIG. 10E shows the effects of AP1 treatment on activation and expression of JNK with Western blotting analysis. FIG. 10F shows the effects of AP1 treatment on activation and expression of PI3K with Western blotting analysis. FIG. 10G shows the effects of AP1 treatment on activation and expression of Akt with Western blotting analysis. FIG. 10H shows the effects of AP1 treatment on eNOS with Western blotting analysis. FIG. 10I shows the effects of AP1 treatment on iNOS with Western blotting analysis.

FIG. 13A shows the flow cytometry pattern of normal (untreated) cells. FIG. 13B shows the flow cytometry pattern of cells of the H/R group. FIG. 13C shows the flow cytometry pattern of cells treated with AP1 at the concentration of 50 µg/mL and exposed to an H/R injury. FIG. 13D shows the flow cytometry pattern of cells treated with AP1 at the concentration of 200 µg/mL and exposed to an H/R injury. FIG. 13E shows the flow cytometry pattern of cells treated with 100 µM diazoxide (DZ) and exposed to an H/R injury. FIG. 13F shows the apoptosis rate of untreated cells, cells of the H/R group and cells treated with 50 µg/mL or 200 µg/mL of AP1 or 100 µM DZ and exposed to an H/R injury.

FIG. 14A shows the fluorescence pattern revealed with normal (untreated) cells. FIG. 14B shows the fluorescence pattern revealed with cells of the H/R group. FIG. 14C shows the fluorescence pattern revealed with cells treated with 50 µg/mL of AP1 and exposed to an H/R injury. FIG. 14D shows the fluorescence pattern revealed with cells treated with 200 µg/mL of AP1 and exposed to an H/R injury. FIG. 14E shows the fluorescence pattern revealed with cells treated with 100 µM DZ and exposed to an H/R injury. FIG. 14F is a diagram showing the mitochondrial membrane potential of cells of the normal, the H/R group and of cells treated with 50 µg/mL or 200 µg/mL of AP1 or 100 µM DZ and exposed to an H/R injury.

DETAILED DESCRIPTION OF THE INVENTION

Figure 1A:
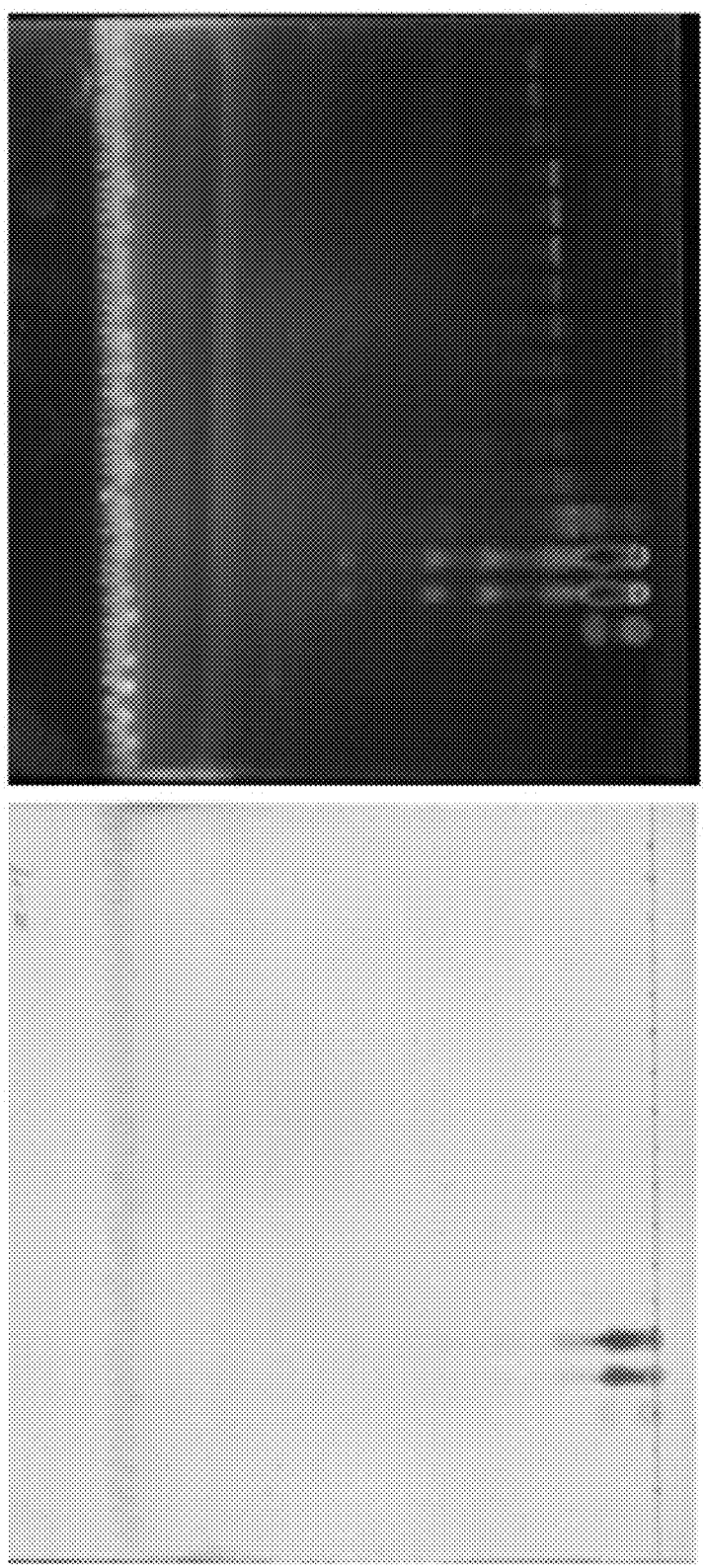
FIGS. 1A, 1B, and 1C show thin-layer chromatography (TLC) spectra of 50 fractions of a crude *Panax ginseng* extract further referred to as standardized *Panax ginseng* extract (RSE) in high-speed counter-current chromatographic (HSCCC) separation.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention provides a method of treating a subject suffering from an ischemic condition. In a further aspect, the present invention provides a method of preventing an ischemia-reperfusion injury in a subject suffering from an ischemic condition.

The term "ischemic condition" as used herein refers to an inadequate or stopped flow and supply, respectively, of blood and oxygen to a part of the body, in particular to an organ and/or tissue caused by constriction or blockage of the blood vessels supplying it with blood such as due to a surgery, an injury or atherosclerotic stenosis, thrombosis, embolism, thromboembolism, or stroke or the like. In particular, the organ is the heart or the tissue is part of the heart, i.e. the ischemic condition preferably refers to an inadequate or stopped flow and supply, respectively, of blood and oxygen to the heart or parts thereof such as to the heart muscle or parts thereof, i.e. the ischemic condition is preferably an ischemic condition affecting the heart.

The ischemic condition is more preferably ischemic heart disease (IHD), also known as coronary artery disease or coronary heart disease, usually caused by a constriction or blockage of the coronary arteries resulting in a reduced blood and oxygen supply to the heart muscle or parts thereof.

The term "ischemia-reperfusion injury" refers to the cellular damage after reperfusion of previously ischemic organs or tissues, i.e. when blood and oxygen supply returns to the tissue after a period of ischemia. More specifically, the restoration of blood flow after an ischemic condition can actually be more damaging than the ischemic condition itself. The so called ischemia-reperfusion injury can result in acceleration of cell death. The absence of oxygen and nutrients from blood creates a condition in which the restoration of blood supply results in inflammation and oxidative damage through the induction of oxidative stress leading to the ischemia-reperfusion injury.

Said methods of the present invention comprise administering an effective amount of a carbohydrate composition extracted from *Panax ginseng* to the subject.

The subject can be an animal or a human. Preferably, the subject is a mammal, in particular the subject is a human.

The term "carbohydrate composition" as used herein means a composition comprising significant amounts, in particular more than 50% by weight, of carbohydrates, in particular polysaccharides, and more preferably more than 70% by weight and especially preferably more than 80% by weight and most preferably more than 85% by weight or even at least 90% by weight of carbohydrates. The total amount of carbohydrates is also referenced herein as the "carbohydrate portion" of the carbohydrate composition. I.e. the carbohydrate composition extracted from *Panax ginseng* comprises a carbohydrate portion, preferably formed by at least one polysaccharide, with an amount of more than 50% by weight, preferably more than 70% by weight and more preferably more than 80% by weight and most preferably more than 85% by weight or even at least 90% by weight based on the weight of the carbohydrate composition.

The term "carbohydrates" as used herein comprises monosaccharides including functionally modified monosaccharides, i.e. monosaccharides carrying functional groups like carboxyl groups, ester groups or amino groups, as well as polysaccharides formed by the monosaccharides and/or functionally modified monosaccharides. Polysaccharides as used herein are polymeric carbohydrates composed of two or more monosaccharides and/or functionally modified monosaccharides which are bound together usually by glycosidic linkage. A polysaccharide might further contain amino acids or polypeptides linking such as cross-linking components of the polysaccharide. This is still referred to as one polysaccharide according to this invention, wherein the linking such as cross-linking amino acids/polypeptides form the protein portion and the monosaccharides and polysaccharide components linked such as cross-linked by the amino acids/polypeptides form part of the carbohydrate portion of the carbohydrate composition.

The monosaccharides of a polysaccharide can be identical in which case the polysaccharide is referenced as a homopolysaccharide or homoglycan. If more than one type of monosaccharide is present in the polysaccharide, such polysaccharide is referenced as heteropolysaccharide or heteroglycan. A polysaccharide can, for example, be basic, neutral or acidic depending on the functional groups the monosaccharides of the polysaccharide carry. Acidic polysaccharides are generally polysaccharides that comprise monosaccharides carrying functional groups which can release protons such as carboxyl groups, phosphate groups and/or sulfate groups. Basic polysaccharides can be proton acceptors due to functional groups of monosaccharides such as amino groups.

In preferred embodiments of the present invention, the carbohydrate composition comprises at least one polysaccharide. The polysaccharide is most preferably an acidic heteroglycan. In particular embodiments of the present invention, the carbohydrate portion of the carbohydrate composition comprises a polysaccharide which is an acidic heteroglycan, herein said carbohydrate portion amounts to more than 85% by weight and in particular at least 90% by weight of the carbohydrate composition.

The molecular weight of the at least one polysaccharide in the carbohydrate composition may be, for example, between 10,000 Da and 80,000 Da, in particular about 20,000 Da to 60,000 Da, most preferably about 38,000 Da.

Preferred monosaccharides of the carbohydrate portion which are optionally further functionally modified include one or more monosaccharides selected from the group consisting of glucose, galactose, galacturonic acid, arabinose, xylose, mannose, rhamnose and glucuronic acid, most preferably from one or more of glucose, galactose, galacturonic acid, arabinose and/or glucuronic acid and in particular the carbohydrate portion comprises each of optionally functionally modified glucose, galactose, galacturonic acid, arabinose and glucuronic acid. Preferably, glucose and galactose are the main monosaccharides in the carbohydrate portion, in particular the main monosaccharides forming the at least one polysaccharide.

The carbohydrate composition preferably comprises a carbohydrate portion with a content of more than 80% by weight and further preferred more than 85% by weight based on the weight of the carbohydrate composition, which carbohydrate portion comprises at least 50% by weight of glucose and at least 5% by weight of galactose based on the weight of the carbohydrate portion.

The carbohydrate composition preferably has an uronic acid content of between 1% and 25% by weight based on the weight of the carbohydrate composition, more preferably 4% to 18% by weight in particular determined using the m-hydroxydiphenyl method as described by Blumenkrantz and Asboe-Hansen (Blumenkrantz, N. and Asboe-Hansen, G., Anal Biochem 54, 484-489, 1973). The content of the carbohydrate portion, i.e. the sugar content, can be determined by means of phenol-$H_2SO_4$ colorimetric method (Dubois, M. et al., Analytical chemistry 28, 350-356, 1956).

The carbohydrate composition may comprise further components in addition to the carbohydrate portion, such as a protein portion consisting of amino acids or polypeptides comprising two or more amino acids such as polypeptides linking mono- or polysaccharide components. The protein portion can comprise, for example, one or more of aspartic acid, threonine, serine, glutamic acid, glycine, alanine, valine, methionine, isoleucine, leucine, tyrosine, phenylalanine, lysine, histidine and/or arginine and polypeptides comprising one or more of those amino acids. The carbohydrate composition may have a protein portion with a content of up to 20% by weight based on the carbohydrate composition, preferably up to 15% by weight and in particular less than 10% by weight based on the weight of the carbohydrate composition. The protein content can be determined using a Bio-Rad protein assay kit and BSA as standard.

In preferred embodiments of the present invention, the carbohydrate portion comprises 60% to 80% by weight of glucose, 2% to 22% by weight of galactose, 0.5 to 15% by weight of galacturonic acid, 0.1% to 15% by weight of arabinose and 0.1% to 10% by weight of glucuronic acid based on the weight of the carbohydrate portion. In further preferred embodiments of the present invention, the carbohydrate portion comprises 70% to 80% by weight of glucose, 8% to 18% by weight of galactose, 0.5% to 10% by weight of galacturonic acid, 0.1% to 8% by weight of arabinose and 0.1% to 5% by weight of glucuronic acid based on the weight of the carbohydrate portion.

In a further preferred embodiment of the present invention, the carbohydrate composition comprises about 90.28% by weight of a carbohydrate portion with about 76.31% by weight of glucose, about 12.70% by weight of galactose, about 5.64% by weight of galacturonic acid, about 3.72% by weight of arabinose and about 1.64% by weight of glucuronic acid and the rest of the carbohydrate composition being a protein portion, i.e. up to about 9.85% by weight based on the carbohydrate composition.

As used herein the term "extracted from *Panax ginseng*" means that the carbohydrate composition is derived, namely derived by means of extraction including further processing and purification from *Panax ginseng* plant material. The term "extraction" will be understood by those skilled in the art as treating plant material with an extraction solvent to obtain desired components, in the present invention carbohydrates, and separating them from unwanted plant material and/or other components present in the plant material. The carbohydrate composition extracted from *Panax ginseng* can be in liquid form, in particular a decoction, solution, infusion or tincture or in solid form, in particular a powder or granules. Most preferably, the carbohydrate composition is in solid form, in particular a powder, most preferably a dried such as freeze-dried powder.

The carbohydrate composition can be administered in combination with other therapeutic compounds, preferably therapeutic compounds used for treating ischemic conditions, in particular used for treating ischemic heart disease such as for preventing an ischemia-reperfusion injury.

By "effective amount" is meant the safe and efficacious amount required to therapeutically treat or ameliorate a condition, such as an ischemic condition or an ischemia-reperfusion injury, i.e. to treat the condition in a clinically relevant manner. The effective amount may vary depending upon the subject, the kind of administration, age, and general health of the subject and can be determined by standard procedures such as with cell cultures or experimental animals. A concentration of the carbohydrate composition may, for example, be between 1 μg/ml and 800 μg/ml, such as between 6.25 μg/ml and 800 μg/ml and in particular of from about 50 μg/ml to about 200 μg/ml, most preferably about 200 μg/ml.

The carbohydrate composition can be administered to the subject alone or as part of a pharmaceutical formulation which further comprises at least one pharmaceutically acceptable excipient and may additionally contain at least one further therapeutic compound, in particular a therapeutic compound for treating ischemic conditions such as ischemic heart disease.

The skilled person is able to select suitable excipients depending on the form of the pharmaceutical formulation and is aware of methods for manufacturing pharmaceutical formulations as well as able to select a suitable method for preparing the pharmaceutical formulation depending on the kind of excipients and the form of the pharmaceutical formulation. Preferred pharmaceutically acceptable excipients include one or more of a salt, buffer, water, a diluent, a filler, a binder, a disintegrant, a lubricant, a coloring agent, a surfactant and/or a preservative.

The pharmaceutical formulation according to the invention can be present in solid, semisolid or liquid form to be administered by an oral, rectal, topical, parenteral or transdermal or inhalative route to a subject, preferably a human. Preferably, the pharmaceutical formulation is for oral administration to the subject.

In preferred embodiments of the present invention, the carbohydrate composition is obtained or obtainable from *Panax ginseng* with an extraction comprising steps of:

(i) providing a crude *Panax ginseng* extract comprising contacting *Panax ginseng* plant material with an extraction solvent comprising an aliphatic alcohol; and (ii) isolating the carbohydrate composition from the crude *Panax ginseng* extract of step (i).

The *Panax ginseng* plant material may comprise the whole plant, i.e. roots, rhizomes and aerial parts like stems and leaves of *Panax ginseng*. Preferably the *Panax ginseng* plant material comprises and in particular essentially consists of the roots of *Panax ginseng* including main and lateral roots.

The method of the present invention may further comprise steps before carrying out step (i) of:

a) drying the *Panax ginseng* plant material, and/or b) cutting, shredding, milling and/or pulverizing the *Panax ginseng* plant material.

The extraction solvent in step (i) preferably comprises an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol is a monohydric aliphatic alcohol, still more preferably a monohydric alcohol with 1 to 3 carbon atoms. I.e. the aliphatic alcohol is more preferably selected from methanol, ethanol, propanol or isopropanol or mixtures thereof. More preferably, the aliphatic alcohol is ethanol. The extraction solvent in step (i) most preferably essentially consists of up to about 70 Vol.-% ethanol, preferably of from about 50 Vol.-% ethanol to about 70 Vol.-% ethanol.

Step (i) preferably comprises steps of:

a) contacting the *Panax ginseng* plant material with the extraction solvent for obtaining a mixture of *Panax ginseng* plant material and extraction solvent;

b) subjecting the mixture of step a) to one or more of stirring, shaking, heating to a temperature of more than 30° C., sonication like ultrasonication and/or allowing the mixture of step a) to stand at a temperature of between 20° C. and 30° C., more preferably of about 25±2° C.

c) isolating the crude *Panax ginseng* extract such as by one or more of filtering the mixture after step b) and/or at least partially removing the extraction solvent after step b) by concentrating the mixture optionally after filtration such as under vacuum and/or by drying such as freeze-drying. Preferably, step c) comprises filtering the mixture after step b), concentrating the mixture after filtration preferably under vacuum and drying such as freeze-drying the concentrated filtrate. Drying is preferably carried out under low temperatures such as below 30° C.

Step a) more preferably comprises contacting the *Panax ginseng* plant material with about 5 volumes (vs. weight of the *Panax ginseng* plant material) of about 50 Vol.-% to about 70 Vol.-% ethanol as extraction solvent.

Step b) more preferably comprises subjecting the mixture of step a) to one or more of stirring, shaking, sonication like ultrasonication and/or allowing it to stand at a temperature of between 20° C. and 30° C., more preferably at about 25±2° C., in particular for at least 30 min, more preferably for about 2 h.

Preferably, step (i) is repeated at least two times and most preferably about three times with the same *Panax ginseng* plant material. I.e. the *Panax ginseng* plant material is subjected to steps a) and b) at least two and preferably three times, wherein the isolated crude *Panax ginseng* extracts are combined.

In especially preferred embodiments of the present invention, the *Panax ginseng* plant material is subjected to step a) by contacting the *Panax ginseng* plant material with about 5 volumes (vs. weight of *Panax ginseng* plant material) of about 50 Vol.-% to about 70 Vol.-% ethanol and step b) by subjecting the mixture of step a) to one or more of stirring, shaking, sonication like ultrasonication and/or allowing it to stand at a temperature of between 20° C. and 30° C. for about 2 h and the mixture of step b) is then subjected to filtration in step c) for obtaining a first filtrate and a first residue. The first residue comprising *Panax ginseng* plant material is again subjected to the steps a) and b) as described above and a second filtrate and a second residue is obtained in step c) by filtration. The second residue is again subjected to the steps a) and b) as described above for forming a third filtrate and a third residue after filtration in step c). The first, second and third filtrate are combined, concentrated and finally dried under low temperatures to form a powder as crude *Panax ginseng* extract in step c).

The crude *Panax ginseng* extract obtained in step (i) is preferably a standardized *Panax ginseng* extract, i.e. is standardized to contain a predetermined amount of ginsenosides. The crude *Panax ginseng* extract obtained in step (i) preferably comprises ginsenosides Rg1, Re, Rb1, Rc, Rb2 and Rd with amounts of:

about 6.5 to 9.7 mg/g, more preferably about 8.08 mg/g of Rg1;

about 6.1 to 9.2 mg/g, more preferably about 7.64 mg/g of Re;

about 9.3.0 mg/g to 13.9 mg/g, more preferably about 11.58 mg/g of Rb1;

about 8.3 mg/g to 12.4 mg/g, more preferably about 10.35 mg/g of Rc;

about 5.3 mg/g to 8.0 mg/g, more preferably about 6.67 mg/g of Rb2;

and about 3.6 to 5.4 mg/g, more preferably about 4.50 mg/g of Rd.

The above mentioned ginsenosides and methods for their determination are known to the skilled person, e.g. from Zheng et al. and Zhou et al. (Zheng, S.-D. et al., Chinese journal of integrative medicine 18, 548-555, 2012, Zhou, H. et al., J Ethnopharmacol 135, 287-298, 2011). In particular, the amount of ginsenosides can be determined by means of high-performance liquid chromatography (HPLC) coupled with time of flight mass spectrometer (HPLC-TOF-MS) and respective standards.

The crude *Panax ginseng* extract obtained in step (i) most preferably comprises ginsenosides Rg1, Re, Rb1, Rc, Rb2 and Rd with amounts of about 8.08 mg/g, about 7.64 mg/g, about 11.58 mg/g, about 10.35 mg/g, about 6.67 mg/g and about 4.50 mg/g, respectively.

Step (ii) of isolating the carbohydrate composition from the crude *Panax ginseng* extract of step (i) preferably comprises steps of:

a) optionally fractionating the crude *Panax ginseng* extract for obtaining a carbohydrate-enriched *Panax ginseng* extract;

b) adding water and an aliphatic alcohol to the crude *Panax ginseng* extract of step (i) or the carbohydrate-enriched *Panax ginseng* extract of step a) if said step a) is carried out for obtaining a carbohydrate-enriched precipitate;

c) subjecting the carbohydrate-enriched precipitate to an anion-exchange chromatography with an eluting solvent for obtaining an eluate comprising the carbohydrate composition;

d) concentrating the eluate of step c) for obtaining the carbohydrate composition.

The term "fractionating" means separating the components present in the crude *Panax ginseng* extract into more than two fractions with different composition, namely a different kind and/or number of components initially present in the crude *Panax ginseng* extract. This allows obtaining fractions with an increased amount of carbohydrates, i.e. carbohydrate-enriched fractions which are combined for forming the carbohydrate-enriched *Panax ginseng* extract.

Step a) is preferably carried out by means of fluid-fluid chromatography and/or fluid-solid chromatography, in particular fluid-fluid chromatography and fluid-solid chromatography. In most preferred embodiments, the fluid chromatography is carried out as a high-speed counter-current chromatography (HSCCC) and the fluid-solid chromatography is carried out as a high-performance liquid chromatography (HPLC), wherein HSCCC is preferably followed by HPLC. In preferred embodiments of the present invention, fractionating the crude *Panax ginseng* extract in step a) comprises subjecting the crude *Panax ginseng* extract to fluid-fluid chromatography, wherein the fluid-fluid chromatography is carried out as high-speed counter-current chromatography.

HSCCC is preferably carried out with a TBE-1000A HSCCC system equipped with a three polytetrafluoroethylene coil with 1000 mL total capacity. The β value of the column from internal layer to external layer can vary from 0.59 to 0.75. A HPLC is preferably connected to the HSCCC. The diphase solvent system used for the HSCCC is preferably prepared by adding the solvent system components to a separation funnel according to the desired volume ratio and repeatedly shaking at room temperature, i.e. at a temperature of about 25±2° C. The upper and lower phases are preferably separated, degassed by sonication, and settled over night before use.

The two-phase solvent system of the HSCCC preferably comprises one or more of an aliphatic alcohol, water and an ester. The ester is in particular a $C_1$-$C_6$ aliphatic alcohol ester of a $C_1$-$C_7$ alkyl carboxylic acid. Further preferably, the ester is a $C_3$-$C_7$ ester, in particular ethyl acetate. The aliphatic alcohol is preferably a monohydric aliphatic alcohol, in particular an aliphatic alcohol with 3 or more carbon atoms, most preferably n-butanol. The two-phase solvent system most preferably comprises at least two of n-butanol, water and ethyl acetate. Further preferably, a first two phase solvent system comprising n-butanol and water is used and a second two phase solvent system comprising ethyl acetate and water.

The crude *Panax ginseng* extract is preferably dissolved in the two-phase solvent system, centrifuged preferably at 4000 rpm preferably for about 15 min to obtain a supernatant as sample solution. The HSCCC column is preferably filled with the upper layer of butanol-water at a ratio of 1:1, then rotated in "forward" direction preferably at 800 rpm and the crude *Panax ginseng* extract is preferably injected into the column through the injection loop. Preferably, the lower phase of butanol-water (1:1) is then pumped into the column in a "head to tail" mode at a flow rate of preferably 8 mL/min. When the separation time ran to 100 min, the mobile phase is preferably changed to the lower phase of ethyl acetate-water (1:1). Fractions are preferably collected in 5 min intervals.

Fractions with an increased amount of carbohydrates according to a thin-layer chromatography (TLC) analysis are preferably combined further referenced as carbohydrate-enriched *Panax ginseng* extract which may be concentrated by means of drying such as freeze-drying. The thin-layer chromatography is preferably carried out with silica gel, in particular silica gel 60, developed with chloroform/methanol/water (13:7:2) and detected under UV-254 nm. The presence of carbohydrates can be verified with usual and well-known reagents such as p-anisidine hydrochloride, naphthoresorcinol with acid or silver nitrate with base. In particular preferred embodiments of the present invention, the carbohydrate-enriched *Panax ginseng* extract is obtained by drying such as freeze-drying combined fractions comprising an increased amount of carbohydrates.

The aliphatic alcohol used in step b) is an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol is a monohydric aliphatic alcohol, still more preferably a monohydric alcohol with 1 to 3 carbon atoms. I.e. the aliphatic alcohol is more preferably selected from methanol, ethanol, propanol or isopropanol or mixtures thereof. More preferably, the aliphatic alcohol is ethanol. The amount of water and aliphatic alcohol, in particular ethanol, can be selected such that a mixture with 70 Vol.-% to 90 Vol.-%, in particular about 70 Vol.-% aliphatic alcohol in water is obtained. Preferably, the crude *Panax ginseng* extract of step (i) or the carbohydrate-enriched *Panax ginseng* extract of step a) is dissolved in water and then the aliphatic alcohol optionally with water is added for obtaining a concentration of 70 Vol.-% to 90 Vol.-% aliphatic alcohol in water, in particular about 70 Vol.-% aliphatic alcohol in water. The aliphatic alcohol is more preferably ethanol, and water and ethanol are added such that an ethanol concentration of about 70 Vol.-% is obtained.

Step b) in particular further comprises a step of separating the precipitate such as by filtration preferably after 12 h, more preferably after about 24 h and/or by centrifugation. The precipitate may be further purified such as by washing with a washing solvent and/or by drying such as freeze-drying.

The anion-exchange chromatography in step c) is preferably carried out with an anion exchange resin comprising diethylamino ethyl groups (DEAE), most preferably with a DEAE-650 M column. The eluting solvent in step c) preferably comprises one or more of water, sodium hydroxide and sodium chloride, in particular water and sodium chloride. The eluting solvent can in particular embodiments of the present invention be selected from water, 0.5 M to 2 M sodium chloride or 0.2 M sodium hydroxide, most preferably water and 0.5 M sodium chloride.

Concentrating the eluate in step d) in particular includes one or more of at least partially removing the eluting solvent, dialysis, centrifugation and/or drying such as freeze-drying, most preferably each of them. Preferably concentrating the eluate in step d) comprises removing the eluting solvent at least partially from the eluate such as by evaporating the eluting solvent under reduced pressure for obtaining a residue, dialyzing the residue in particular in water for at least 12 h, in particular for about 24 h such as against a 1,000 Da sieve, optionally centrifuging the dialyzed residue and freeze-drying.

In embodiments of the present invention, step (ii) comprises and in particular consists of steps a) to d), i.e. comprises and in particular consists of steps of:
fractionating the crude *Panax ginseng* extract for obtaining a carbohydrate-enriched *Panax ginseng* extract in particular comprising high-speed counter-current chromatography;
adding water and an aliphatic alcohol, in particular ethanol, to the carbohydrate-enriched *Panax ginseng* extract of the preceding step for obtaining a carbohydrate-enriched precipitate;
subjecting the carbohydrate-enriched precipitate to an anion-exchange chromatography with an eluting solvent, in particular comprising water and sodium chloride, for obtaining an eluate with the carbohydrate composition;
concentrating the eluate of the preceding step comprising at least partially removing the eluting solvent for obtaining residue, dialyzing the residue in water, optionally centrifuging the dialyzed mixture and freeze-drying.

In alternative embodiments of the present invention, step (ii) comprises and in particular consists of steps b) to d), i.e. comprises and in particular consists of steps of:
adding water and an aliphatic alcohol, in particular ethanol, to the crude *Panax ginseng* extract of step (i) for obtaining a carbohydrate-enriched precipitate;
subjecting the carbohydrate-enriched precipitate to an anion-exchange chromatography with an eluting solvent, in particular comprising water and sodium chloride, for obtaining an eluate with the carbohydrate composition;
concentrating the eluate of the preceding step comprising at least partially removing the eluting solvent for obtaining residue, dialyzing the residue in water, optionally centrifuging the dialyzed mixture and drying such as freeze-drying.

In most preferred embodiments of the present invention, step (ii) consists of steps b) to d), i.e. of steps of:
adding water and an aliphatic alcohol, in particular ethanol, to the crude *Panax ginseng* extract of step (i) for obtaining a carbohydrate-enriched precipitate;
subjecting the carbohydrate-enriched precipitate to an anion-exchange chromatography with an eluting solvent, in particular comprising water and sodium chloride, for obtaining an eluate with the carbohydrate composition;
concentrating the eluate of the preceding step comprising at least partially removing the eluting solvent for obtaining residue, dialyzing the residue in water, optionally centrifuging the dialyzed mixture and drying such as freeze-drying.

In another aspect, the present invention provides a method of protecting cells against hypoxia and reoxygenation induced cell death. The method comprises contacting the cells with a carbohydrate composition extracted from *Panax ginseng*.

The carbohydrate composition and the extraction from *Panax ginseng* are as described above. The concentration of the carbohydrate composition used for contacting the cells is preferably between 1 µg/ml and 800 µg/ml, in particular between 6.25 µg/ml and 800 µg/ml, most preferably the concentration of the carbohydrate composition used for contacting the cells is of from about 50 µg/ml to about 200

µg/ml, most preferably of about 200 µg/ml. The cells are contacted with the carbohydrate composition preferably for at least 12 h, more preferably for about 24 h.

The step of contacting the cells with the carbohydrate composition of the present invention may be carried out by applying an incubation solution comprising the carbohydrate composition to said cells which incubation solution may further comprise suitable excipients such as one or more of a buffer, water or a suitable growth medium. In another embodiment of the present invention, contacting the cells with the carbohydrate composition comprises administering an effective amount of the carbohydrate composition to a subject, which subject comprises said cells. The carbohydrate composition may be administered in form of a pharmaceutical formulation as described above and optionally in combination with at least one further therapeutic compound, in particular a therapeutic compound for treating ischemic conditions such as ischemic heart disease.

The cells are preferably cardiomyocytes, i.e. from the cardiac muscle.

The expression "protecting cells against hypoxia and reoxygenation induced cell death" means an increased cell viability and reduced apoptosis rate compared to untreated cells of the same cell and tissue type. Protecting the cells against hypoxia and reoxygenation induced cell death in particular means that the cell viability is significantly increased compared to the cell viability of untreated cells exposed to hypoxia and regoxygenation. The cell viability compared to normoxic cells, i.e. cells not exposed to hypoxia and regoxygenation is preferably less than 20% decreased, more preferably less than 15%, more preferably less than 10% and further preferable less than 5%, in particular less than 2% when contacting the cells with the carbohydrate composition of the present invention preferably at least 30 min, in particular about 1 h before and during the exposure to hypoxic conditions and regoxygenation. The cell viability can be determined, for example, by means of a mitochondrial viability stain (MVS) assay (e.g. Sathishkumar, K. et al., Free Radicals and Antioxidant Protocols, 51-61, 2010). The assay can be carried out by overlaying treated and untreated cells with mitochondrial viability stain and then incubating them under normoxic conditions (95% air/5% $CO_2$) for 4 h in the dark. The fluorescent intensity can be measured at excitation 550 nm and emission 590 nm.

A reduced apoptosis means a significantly decreased apoptosis under the treatment compared to untreated cells exposed to hypoxia and regoxygenation. The apoptosis rate is preferably not more than 30%, further preferred not more than 20% increased compared to normoxic cells, more preferred not more than 15% and in particular not more than 10% increased compared to normoxic cells when contacting the cells with the carbohydrate composition of the present invention preferably at least 30 min, in particular about 1 h before and during the exposure to hypoxic conditions and regoxygenation. Apoptosis can be determined by means of flow cytometry/Annexin V assay.

Contacting the cells, in particular cardiomyocytes, with the carbohydrate composition in particular has at least one of the following effects: prevents morphological changes of the cells, protects the mitochondrial function such as by increasing the mitochondrial membrane potential, increases the ATP level, increases the Bcl-2/Bax ratio and activates the pro-survival Reperfusion Injury Salvage Kinase (RISK) Pathway. This can be determined such as by measuring the levels of Erk1/2/phospho-Erk1/2, PI3K/phospho-PI3K, Akt/phospho-Akt, and/or eNOS/phosphor-eNOS such as by means of Western Blotting.

The carbohydrate composition for contacting the cells preferably comprises a carbohydrate portion with a content of more than 85% by weight based on the weight of the carbohydrate composition and wherein the carbohydrate portion comprises 70% to 80% by weight of glucose, 8% to 18% by weight of galactose, 0.5% to 10% by weight of galacturonic acid, 0.1% to 8% by weight of arabinose and 0.1% to 5% by weight of glucuronic acid based on the weight of the carbohydrate portion. The carbohydrate composition in particular comprises at least one polysaccharide which is an acidic heteroglycan.

Further provided is a method for preparing a carbohydrate composition by extracting the carbohydrate composition from *Panax ginseng* as described above.

The present invention further refers to the carbohydrate composition extracted from *Panax ginseng*, i.e. obtainable or obtained by the extraction described above, in particular comprising at least on polysaccharide which is an acidic heteroglycan with a molecular weight of preferably about 20,000 Da to about 60,000 Da, most preferably about 38,000 Da.

The carbohydrate composition preferably comprises a carbohydrate portion with a content of more than 80% by weight, further preferred more than 85% by weight based on the weight of the carbohydrate composition, which carbohydrate portion comprises at least 50% by weight of glucose and at least 5% by weight of galactose based on the weight of the carbohydrate portion.

More preferably, the carbohydrate portion comprises 60% to 80% by weight of glucose, 2% to 22% by weight of galactose, 0.5% to 15% by weight of galacturonic acid, 0.1% to 15% by weight of arabinose and 0.1% to 10% by weight of glucuronic acid based on the weight of the carbohydrate portion.

In further preferred embodiments of the present invention, the carbohydrate portion comprises 70% to 80% by weight of glucose, 8% to 18% by weight of galactose, 0.5% to 10% by weight of galacturonic acid, 0.1% to 8% by weight of arabinose and 0.1% to 5% by weight of glucuronic acid based on the weight of the carbohydrate portion.

Most preferably, the carbohydrate composition comprises about 90.28% by weight of a carbohydrate portion with about 76.31% by weight of glucose, about 12.70% by weight of galactose, about 5.64% by weight of galacturonic acid, about 3.72% by weight of arabinose and about 1.64% by weight of glucuronic acid based on the weight of the carbohydrate portion and the rest of the carbohydrate composition being the protein portion, i.e. up to about 9.85% by weight of a protein portion based on the weight of the carbohydrate composition.

In further preferred embodiments, the carbohydrate composition of the present invention is extracted from, i.e. obtained from *Panax ginseng* comprising steps (i) and (ii) of:

(i) providing a crude *Panax ginseng* extract comprising contacting *Panax ginseng* plant material with an extraction solvent comprising an aliphatic alcohol, in particular ethanol; which step (i) comprises steps of:

a) contacting the *Panax ginseng* plant material with the extraction solvent for obtaining a mixture of *Panax ginseng* plant material and extraction solvent;

b) subjecting the mixture of step a) to one or more of stirring, shaking, heating to a temperature of more than 30° C., sonication like ultrasonication and/or allowing the mixture of step a) to stand at a temperature of between 20° C. and 30° C.;

c) isolating the crude *Panax ginseng* extract such as by one or more of filtering the mixture after step b) and/or at least partially removing the extraction solvent after step b) by concentrating the mixture optionally after filtration such as under vacuum and/or by drying such as freeze-drying. Preferably, step c) comprises filtering the mixture after step b), concentrating the mixture after filtration under vacuum and drying such as freeze-drying the concentrated filtrate;

(ii) isolating the carbohydrate composition from the crude *Panax ginseng* extract of step (i) comprising steps of:

a) optionally fractionating the crude *Panax ginseng* extract for obtaining a carbohydrate-enriched *Panax ginseng* extract in particular comprising high-speed counter-current chromatography;

b) adding water and an aliphatic alcohol, in particular ethanol, to the crude *Panax ginseng* extract of step (i) or the carbohydrate-enriched *Panax ginseng* extract of step a) for obtaining a carbohydrate-enriched precipitate;

c) subjecting the carbohydrate-enriched precipitate to an anion-exchange chromatography with an eluting solvent, in particular comprising water and sodium chloride, for obtaining an eluate comprising the carbohydrate composition;

d) concentrating the eluate of step c) for obtaining the carbohydrate composition.

The crude *Panax ginseng* extract obtained in step (i) most preferably comprises ginsenosides Rg1, Re, Rb1, Rc, Rb2 and Rd with amounts of about 8.08 mg/g, about 7.64 mg/g, about 11.58 mg/g, about 10.35 mg/g, about 6.67 mg/g and about 4.50 mg/g, respectively.

The present invention further provides a pharmaceutical formulation comprising an effective amount of the carbohydrate composition described above and at least one pharmaceutically acceptable excipient such as selected from a diluent, a filler, a binder, a disintegrant, a lubricant, a coloring agent, a surfactant or a preservative. The pharmaceutical formulation according to the invention can be present in solid, semisolid or liquid form to be administered by an oral, rectal, topical, parenteral or transdermal or inhalative route to a subject, preferably a human.

The invention is also the carbohydrate composition described above for use as a medicament for the treatment of an ischemic condition and/or for preventing an ischemia-reperfusion injury in a subject suffering from an ischemic condition, in particular ischemic heart disease. Another aspect of the invention refers to the use of the carbohydrate composition described above for preparing a medicament for treatment of an ischemic condition and/or for preventing an ischemia-reperfusion injury in a subject suffering from an ischemic condition, in particular ischemic heart disease. The present invention also relates to the use of the carbohydrate composition as described above for protecting cells against hypoxia and reoxygenation induced cell death, in particular for increasing the cell viability and reducing the apoptosis rate under hypoxic conditions and regoxygenation

EXAMPLES

Deionized water was prepared by Millipore MILLI Q-Plus system (Millipore, Bedford, Mass., USA). ACS grade methanol, chloroform, ethyl acetate and butanol were purchased from ACS Chemical, Inc. (NJ, USA). ACS grade Ethanol, phenol, concentrated sulfuric acid, ammonia water, and sodium hydroxide were purchased from Merck (Darmstadt, GERMANY). Trifluoroacetic acid (TFA) and ammonium acetate were bought from Riedel-de Haen (Morristown, N.J., USA). HPLC grade acetonitrile was purchased from RCL Labscan Limited (Bangkok, Thailand). The monosaccharide standards, D-glucose (Glc), D-galacturonic acid monohydrate (Gal A), 1-pheny-3-methy-5-pyrazolne (PMP), sodium chloride, and dextrans with different molecular weight were purchased from Sigma (St. Louis, Mo., USA).

Mitochondrial Viability Stain (MVS) assay reagent was purchased from Abcam (Cambridge, England, Cat. ab129732). Diazoxide (DZ) was purchased from Sigma (St. Louis, Mo., USA). Dulbecco's modified Eagle's medium (DMEM), glucose-free DMEM, fetal bovine serum (FBS) and trypsin were obtained from Gibco (Carlsbad, Calif. USA). Griess reagent, inhibitor of GR mifepristone, inhibitor of ER tamoxifen, inhibitor of PI3K L29002, Akt inhibitor IV, inhibitor of p-ERK1/2 U0126 and inhibitor of eNOS L-NAME were purchased from Sigma-Aldrich (St. Louis, Mo., USA). All other chemicals were of analytic grade and commercially available.

Example 1

Extraction of a Carbohydrate Composition of the Present Invention

Example 1A

Provision of the crude *Panax ginseng* extract (hereinafter referenced as "RSE") *Panax ginseng* was authenticated, and its quality conformed to the requirements of the Chinese Pharmacopoeia (Edition 2015) and Hong Kong Standard of Chinese Materia *Medica*. The sample was stored in a desiccated condition in the laboratory until use. Voucher specimens in the form of whole root were deposited in the State Key Laboratory of Quality Research in Chinese Medicine (Macau University of Science and Technology). The standardized *ginseng* extract (RSE) was first prepared from *P. ginseng* by extraction for 2 h with 5 volumes (vs. *Panax ginseng* weight) of 70% ethanol for three times, a known method for preparing *ginseng* extract. The ethanol extracts were pooled and concentrated and finally dried to powder (RSE) under low temperature. The extraction rate reached at around 28%, meaning that 1 kg *P. ginseng* produced 280 g of RSE. The chemical fingerprints of RSE were established by using high performance liquid chromatography coupled with time of flight mass spectrometer (HPLC-TOF-MS), which led to the identification and quantification of eleven ginsenosides in conjunction with the use of chemical standards of ginsenosides (HPLC purity >98%) purchased from Chengdu Scholar Bio-Tech Co. Ltd. (Chengdu, China) or National Institute for the Control of Pharmaceutical and Biological Products (Beijing, China). The contents of ginsenosides Rg1, Re, Rb1, Rc, Rb2, and Rd, were 8.08, 7.64, 11.58, 10.35, 6.67, and 4.50 mg/g, respectively (Zhou, H. et al., J Ethnopharmacol 135, 287-298, 2011).

Example 1B

Isolation of the Carbohydrate Composition from the Crude *Panax ginseng* Extract Fractionating the Crude *Panax ginseng* Extract by Means of High-Speed Counter-Current Chromatography The crude *Panax ginseng* extract (RSE) was fractionated using high-speed counter-current chromatography (HSCCC) first. The HSCCC instrument used in this study was a TBE-1000A HSCCC system (Tauto Biotechnique Company, Shanghai, China) equipped with a three polytetrafluoroethylene coil with 1000 mL total capacity. The β value of the column from internal layer to external layer varied from 0.59 to 0.75. A Waters (Waters Corp., MA, USA) high performance liquid chromatography (HPLC) was connected to the HSCCC instrument. HPLC was equipped with Waters 2425 pump, Waters 2489UV detector, Waters FlexInject injector and Waters Fraction Collector III collector. The diphase solvent systems were prepared by adding the solvents to a separation funnel according to the volume ratios and fully equilibrated by shaking repeatedly at room temperature. The upper and lower phases were separated, degassed by sonication, and settled over night before use. The RSE extract (4.12 g) was dissolved in 60 mL of a two-phase solvent, then centrifuged with a Centrifuge 5810 (Eppendorf, Hamburg, Germany) at 4000 rpm for 15 min to get the supernatant solution. Firstly, the HSCCC column was filled with the stationary phase (the upper layer of butanol-water at a ratio of 1:1), then the apparatus was rotated in "forward" direction at 800 rpm and the sample solution was injected into the column through the injection loop. After that, the lower phase of butanol-water (1:1) was pumped into the column in a "head to tail" mode at a flow rate of 8 mL/min. When the separation time ran to 100 min, the mobile phase was changed to lower phase of ethyl acetate-water (1:1). The effluent was collected by every 5 min. The fractions were combined according to the thin-layer chromatography (TLC) analysis, and then freeze-dried. TLC was developed with chloroform/methanol/water (13:7:2) and detected under UV-254 nm. CA, USA).

Stepwise Ethanol Precipitation for Obtaining a Carbohydrate-Enriched Precipitate HSCCC fractions were screened for their bioactivities. The carbohydrate-enriched HSCCC fractions, i.e. the carbohydrate-enriched *Panax ginseng* extract was dissolved in water and carbohydrate-enriched precipitates were obtained using stepwise precipitation in 90%, 80% and 70% of ethanol solutions in turns. Supernatants and precipitates were collected via centrifugation and freeze dying.

Subjecting the Carbohydrate-Enriched Precipitates to an Anion-Exchange Chromatography with $H_2O$, $H_2O$/NaCl or NaOH and Concentrating the Eluate Fractions The carbohydrate-enriched precipitates and supernatants were further screened for their bioactivities and the carbohydrate-enriched precipitates were subjected to anion-exchange chromatography on Toyopearl DEAE 650 M that was stepwise eluted with $H_2O$, 0.5 M of NaCl, 1.0 M of NaCl, 2.0 M of NaCl and 0.2 M of NaOH to give 5 eluate fractions. These five eluate fractions were collected via dialysis (Wako, Osaka, JAPAN), centrifugation, and lyophilization, and represent carbohydrate compositions of the present invention named NP, AP1, AP2, AP3, and AP4, respectively.

Example 1C

Isolation of the Carbohydrate Composition from the Crude *Panax ginseng* Extract without a Step of Fractionating the Crude *Panax ginseng* Extract Crude *Panax ginseng* extract (RSE) was dissolved in water and the solution was added with ethanol to make a 70% ethanol solution and then filtered 24 h later. The carbohydrate-enriched precipitate was collected and dissolved in water to make the water solution of the carbohydrate-enriched precipitate. The water solution of the carbohydrate-enriched precipitate was loaded onto DEAE-650 M column chromatography that was eluted with water and 0.5 M NaCl. The 0.5 M NaCl elution was condensed under reduced pressure, and the condensed solution was dialyzed against 1,000 Da sieve in water for 24 hours. The dialyzed solution was collected and freeze-dried it to obtain the carbohydrate composition referenced herein as AP1.

Example 2

Chemical and Pharmacological Characterization

Example 2A

Chemical characterization of the carbohydrate compositions of example 1 Examination by high-performance gel filtration chromatography (HPGPC) The apparent molecular weights of carbohydrate compositions were determined on Agilent 1100 system (Agilent Technologies, Palo Alto, Calif.) equipped with a Alltech 2000 evaporative light-scattering detector (ELSD), and on two TSK GMPWXL gel filtration columns in series (7.8×300 mm×2) with column temperature maintained at 40° C. 20 mM $CH_3COONH_4$ was used as mobile phase at the flow rate of 0.6 mL/min. The drift tube temperature of ELSD was set at 120° C., the nitrogen flow rate was set at 3.2 L/min and the gain number was set to 4. After filtration, 20 µL solution was injected for analysis. Commercially available T-series dextrans (MW 1, 5, 12, 25, 50, 80, 150, 270, 410, 670 kDa) were used as standard molecular markers.

Monosaccharide Composition Analysis

Carbohydrate compositions (5 mg) were hydrolyzed with 2 M TFA at 120° C. for 2 h in a sealed test tube. The acid was removed under reduced pressure by repeated evaporation with methanol. Then 1 mL water was added to dissolve the hydrolysate. After centrifugation (14,000, 10 min), the 100 µL supernatant was mixed with the same volume of $NH_3$ solution and 200 µL 0.5 M PMP methanol solutions. The mixture was allowed to react at 70° C. for 30 min. After cooling, 100 µL glacial acetic acid and 500 µL chloroform were successively added to neutralize the reaction solution and to remove the excess PMP reagents. The organic phase was discarded after vigorous shaking. The operation was performed 4 times, and the aqueous layer was filtered through a 0.22 µm syringe filter (Vertic Chromatography Co., Ltd., Bangkok, THAILAND) before LC-DAD analysis. The monosaccharide composition was analyzed by HPLC using the reported methods (Xu, J. et al., Anal Bioanal Chem 406, 6409-6417, 2014).

Chemical Analysis

Total sugar contents were determined by phenol-$H_2SO_4$ colorimetric method (Dubois, M. et al., Analytical chemistry 28, 350-356, 1956). Uronic acid contents were determined using m-hydroxydiphenyl method (Blumenkrantz, N. and Asboe-Hansen, G., Anal Biochem 54, 484-489, 1973). Protein content analysis was carried out using a Bio-Rad protein assay kit and BSA was used as the standard.

Example 2B

Pharmacological Characterization

The rat ventricular myocardial cell line H9c2 was obtained from the American Type Culture Collection (ATCC, Rockville, Md., USA) and cultured in DMEM supplemented with 10% fetal bovine serum, 100 U/mL penicillin, 100 µg/mL streptomycin at 37° C. under normoxic condition (95% air/5% $CO_2$). The medium was changed every two days, and the confluent cells were passaged by trypsinization weekly. The cells passaged for three to four times were used for experiments described as below.

Comparisons between different experimental groups were performed using one-way AVOVA and SNK post hoc test with Graph Pad Prism 6.0 software (Graph Pad Software Inc., La Jolla, Calif., USA). The data were expressed as mean±standard deviation (SD). P values less than 0.05 were considered as significant.

All measurements were repeated in three wells, the results are the average of three independent experiments.

Cytotoxicity Test

To examine the myocardial cytotoxicity of AP1 on H9c2 cells under normoxic conditions, the cells were cultured in the absence or presence of AP1 at different concentrations (final concentrations range from 100 µg/mL to 1600 µg/mL).

Hypoxia/Reoxygenation

To examine the effectiveness of RSE and AP1 on H9c2 cells under hypoxia/reoxygenation conditions, the cells were cultured under normoxic conditions (95% air/5% $CO_2$) overnight; then the cells were washed twice with Krebs-Ringer Bicarbonate buffer (composition in mM: NaCl 115, KCl 4.7, $CaCl_2$ 2.5, $KH_2PO_4$ 1.2, $MgSO_4$ 1.2, $NaHCO_3$ 24, HEPES 10; pH 7.4) balanced with $N_2$ at 4° C. for overnight. Aliquots (100 µL) of KRB supplemented with 0.01% (w/v) BSA were added to the cells immediately prior to hypoxia. To create a hypoxia condition, a hypoxic chamber (Stem Cell Technologies, USA) was used to produce an in vitro hypoxia challenge (Chiu, P. Y. et al., Molecular and cellular biochemistry 350, 237-250, 2011). In essence, the cells were placed in the sealed chamber and the chamber was flushed with pure $N_2$ for 5 min at a flow rate of 20 mL/min, then, all sealable connectors were closed. After that, the chamber was transferred to an incubator and the cells in the chamber were subjected to 3 h incubation at 37° C. to induced hypoxia. Reoxygenation was initiated by opening the chamber and then replacing the KRB with fresh DMEM medium, the cells were then cultured in an incubator under normoxic conditions (95% air/5% $CO_2$) at 37° C. for another 4 h.

Drug Treatment

The cells were seeded at the density of $8 \times 10^4$ cells/well in a 96-well plate. The final concentration in assays for the crude *Panax ginseng* extract and the HSCCC fractions was 200 µg/mL, based on that, RSE and its active component (final concentrations range from 6.25 to 800 µg/mL) were added to the culture system 1 h before hypoxia treatment and throughout the reoxygenation period. The control normal group was always maintained in normal DMEM and put in the incubator under normoxic atmosphere (95% air/5% $CO_2$). For pharmaceutical blockages, the cells were treated with mifepristone (an inhibitor of GR, 100 µM), tamoxifen (an inhibitor of ER, 100 µM), L-NAME (an inhibitor of NOS, 10 µM), LY294002 (an inhibitor of PI3K, 40 µM), Akt inhibitor IV (an inhibitor of Akt protein kinase, 10 µM), U0126 (an inhibitor of Erk1/2, 40 µM) right before the pretreatment of AP1 (200 µg/mL). The selection of these inhibitors is based on literatures (Aguilar, D. C. et al., Cardiovasc Toxicol 13, 91-99, 2013, Guo, R. et al., Cellular Physiology and Biochemistry 32, 1668-1680, 2013, Wei, C. D. et al., Lipids Health Dis 11, 135, 2012, Diffley, J. M. et al., Molecular Vision 15, 135-145, 2009, Park, E. S. et al., J Ethnopharmacol 153, 552-560, 2014) and the dosages of these inhibitors were screened to ensure that the pretreatment of inhibitors would not affect the hypoxia/reperfusion injury in H/R group.

Assay for Cell Viability

The cell viability was evaluated by MVS assay (Sathishkumar, K. et al., Free Radicals and Antioxidant Protocols, 51-61, 2010). Briefly, at the end of the cell culture, the cells were overlaid with 100 µL of 2×mitochondrial viability stain in each well containing 100 µL of medium and then incubated under normoxic condition (95% air/5% $CO_2$) for 4 h in the dark. The fluorescent intensity was measured at excitation 550 nm and emission 590 nm by a TECAN Infinite M200 micro plate reader (Tecan, Durham, USA).

Western Blot Analysis

At the end of the cell culture, the cells were harvested after H/R, washed twice with cold PBS, and immersed in lysis buffer which containing 0.5% SDS, 1% Nonidet P-40, 1% sodium deoxycholate, 150 mM NaCl (pH 7.5), and protease inhibitors (Sigma, St. Louis, Mo., USA). The cell lysates were centrifuged at 14,000 g for 20 min at 4° C., and the supernatants were collected and stored at −80° C. Protein concentration was measured using Bradford Protein Assay Kit (Bio-Rad, Hercules, Calif., USA). Equal amounts of protein (40 µg) fractions were loaded onto and separated by 10% or 12% SDS-polyacrylamide gel electrophoresis. Proteins were transferred onto nitrocellulose membranes in Tris-glycine buffer at 80 V for 90 min. Membranes were blocked with 5% skim milk powder in Tris-buffered saline containing 0.1% (v/v) Tween-20 (TBST) at room temperature. Incubation with primary antibody (Cell Signaling Technologies, MA, USA) commenced overnight at 4° C. Afterwards, they were washed thrice with TBST and incubated with secondary antibodies for 1 h at room temperature. The immunoreactive bands were detected using the enhanced ECL method (Millipore, Bedford, Mass.). Densitometric analysis of band intensity was performed using LabImage software (Bio-Rad, Hercules, Calif., USA).

Measurement of Nitric Oxide (NO) Production

The concentration of NO in the culture medium was determined by the Griess reaction with minor changes (Chen, X. P. et al., Journal of Neuroinflammation 9, 2012). At the end of the cell culture, 40 µL cell culture fluid, 10 µL NADPH, and 40 µL basal solution (0.03 M PBS; 1.25 mM glucose-6-phosphate; 400 U/L glucose-6-phosphate dehydrogenase; 200 U/L nitrate reeducates) was incubated in a 96 well microtiter plate for 45 min at room temperature. Next, 50 µL Griess reagent was added and the solution incubated for 20 min in the dark at room temperature. Finally, the absorbance of the samples was measured at 540 nm. Concentrations of NO in the sample were calibrated with a reference standard of sodium nitrite ($NaNO_2$) supplied with the kit and the levels of NO were expressed as µM.

Flow Cytometric Analysis of Cardiomyocyte Apoptosis

The percentage of apoptotic cells measured using the Annexin-V/PI kit for flow cytometry as manufacturer's instruction. At the end of the cell culture, the cells were washed with PBS, centrifuged at 1000 g for 5 min, resuspended in ice-cold PBS, centrifuged at 1000 rpm for 5 min. Cells were re-suspended in 1× binding buffer containing propidium iodide (PI) and FITC-labelled Annexin V and incubated for 15 min at 37° C. in the dark, and analyzed with flow cytometry (FACS Vantage-BD Sciences, USA). The data was analyzed using Flow J software for determining the percent of apoptotic cells.

Determination of Caspase Activity

Caspase-3/7 and -9 activities in H9c2 cells were measured as described previously (Lu, C. et al., J Cerebr Blood F Met 30, 1972-1981, 2010), using a Caspase-Glo assay kit (Promega, Wis.). At the end of the cell culture, the reagents were added to the cell culture in 1:1 dilutions. This reagent causes lysis of the cell and cleavage of the DEVD-aminoluciferin substrate, which is freed and degraded by luciferase enzyme. Thus, a luminescent signal is emitted corresponding to caspase-3/7 and -9 activities.

Measurement of Mitochondrial Membrane Potential (MMP)

MMP was measured using the fluorescent dye rhodamine 123 (Rh123, Molecular Probes, Eugene, Oreg., USA). MMP depolarization resulted in the loss of Rh123 from the mitochondria and a decrease in intracellular fluorescence. At the end of the cell culture, Rh123 was added to cultured cells to achieve a final concentration of 10 μM for 30 min at 37° C. The fluorescence was observed by using confocal laser-scanning microscope.

ATP Content Measurement

The ATP level of the cells was measured by a luminescent ATP detection assay kit (Abcam, Cambridge, UK) according to the manual. The ATP concentrations were collected from duplicate wells of 3 independent experiments and detected by the Infinite M200 pro microplate reader.

Effect of AP1 on Mitochondrial Respiration in H9c2 Cells

The effect of AP1 on mitochondrial respiration was assessed in H9c2 cells using the XFp extracelluar Flux Analyzer (Seahorse Biosciences, Massachusetts, USA) according to a protocol modified after that allows the simultaneous measurement of the oxygen consumption rate (OCR) as an indicator of mitochondrial respiration (Duicu, O. M. et al., Rev Chim-Bucharest 66, 519-522, 2015). H9c2 cells were seeded at 5000 cells/well in Seahorse XFp cell culture miniplates (in duplicate) and pretreated without or with AP1 (200 μg/mL) for 1 h, and then exposed to hypoxia for 3 h followed by reoxygenation for another 4 h. The normal group (Normal) was always maintained in normoxic condition. The sensor cartridge for the XFp analyzer was hydrated in 37° C. non-$CO_2$ incubator at the day before experiment. At the end of cell culture, the incubation media was replaced by unbuffered XF assay medium (provided by Seahorse Co.) containing 2.5 M glucose. OCR rates were measured over the time to establish the baseline rates. Afterwards the cells were metabolically challenged (in order to shift their bioenergetic profile) by three successive additions: oligomycin (10 μM), FCCP (2 μM), and Rotenone & antimycin A (0.5 μM). Previous studies were performed to optimize the cell seeding density and the FCCP concentrations, respectively (data not shown). Background correction wells (i.e., wells that were not seeded with cells) were included in the assay to normalize the data to the background plate noise. The following OCR parameters were recorded: (1) the basal respiration of the cells; (2) the percent of $O_2$ consumption required for the ATP production (ATP turnover); (3) the amount of $O_2$ consumption devoted to maintain the proton gradient (proton leak); (4) the maximal respiratory rate under conditions of uncoupled respiration. For further analysis, mitochondrial parameters were corrected to the non-mitochondrial respiration and instrumental background. OCR was reported in units of pmol/min/μg protein.

Results

Figure 1B:
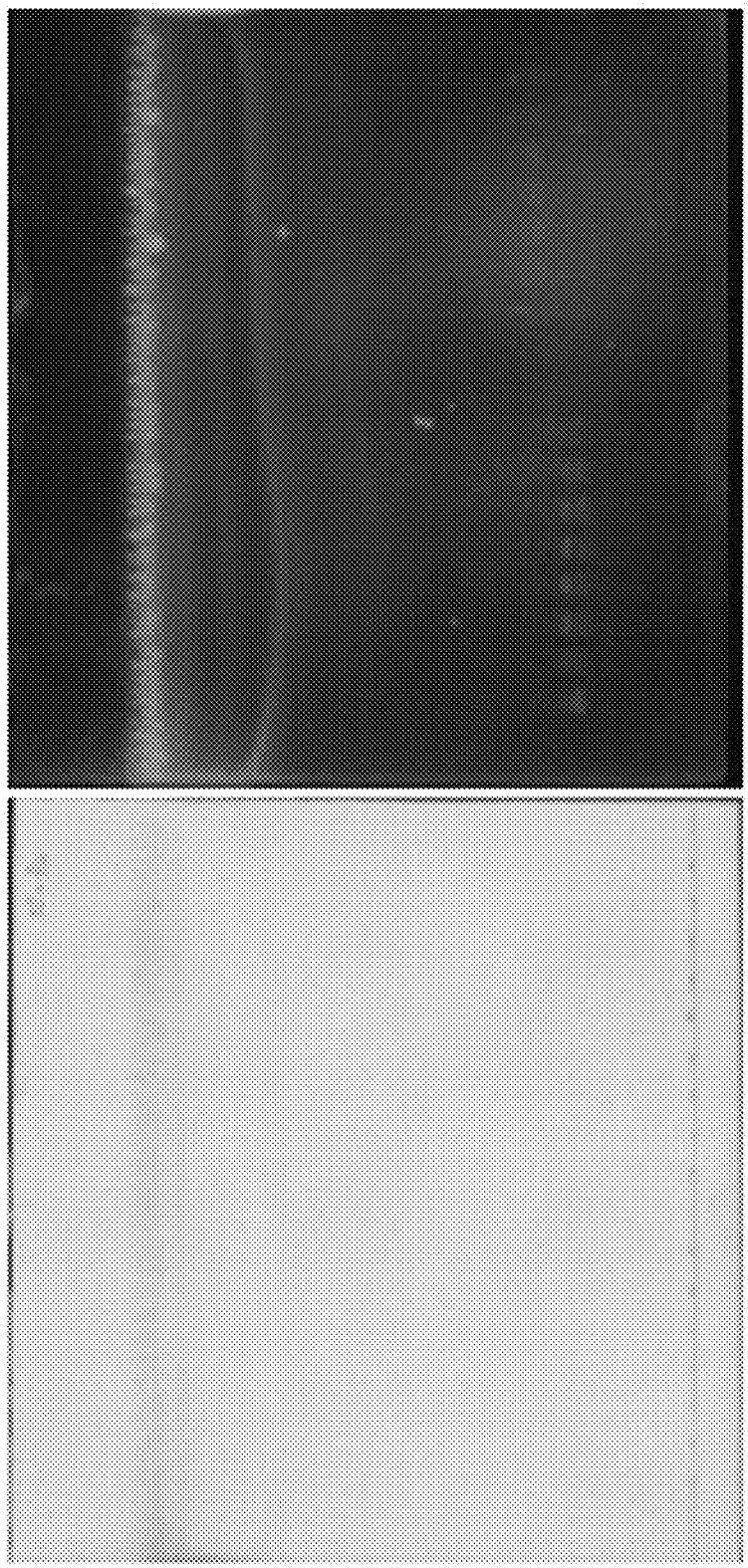
Figure 1C:
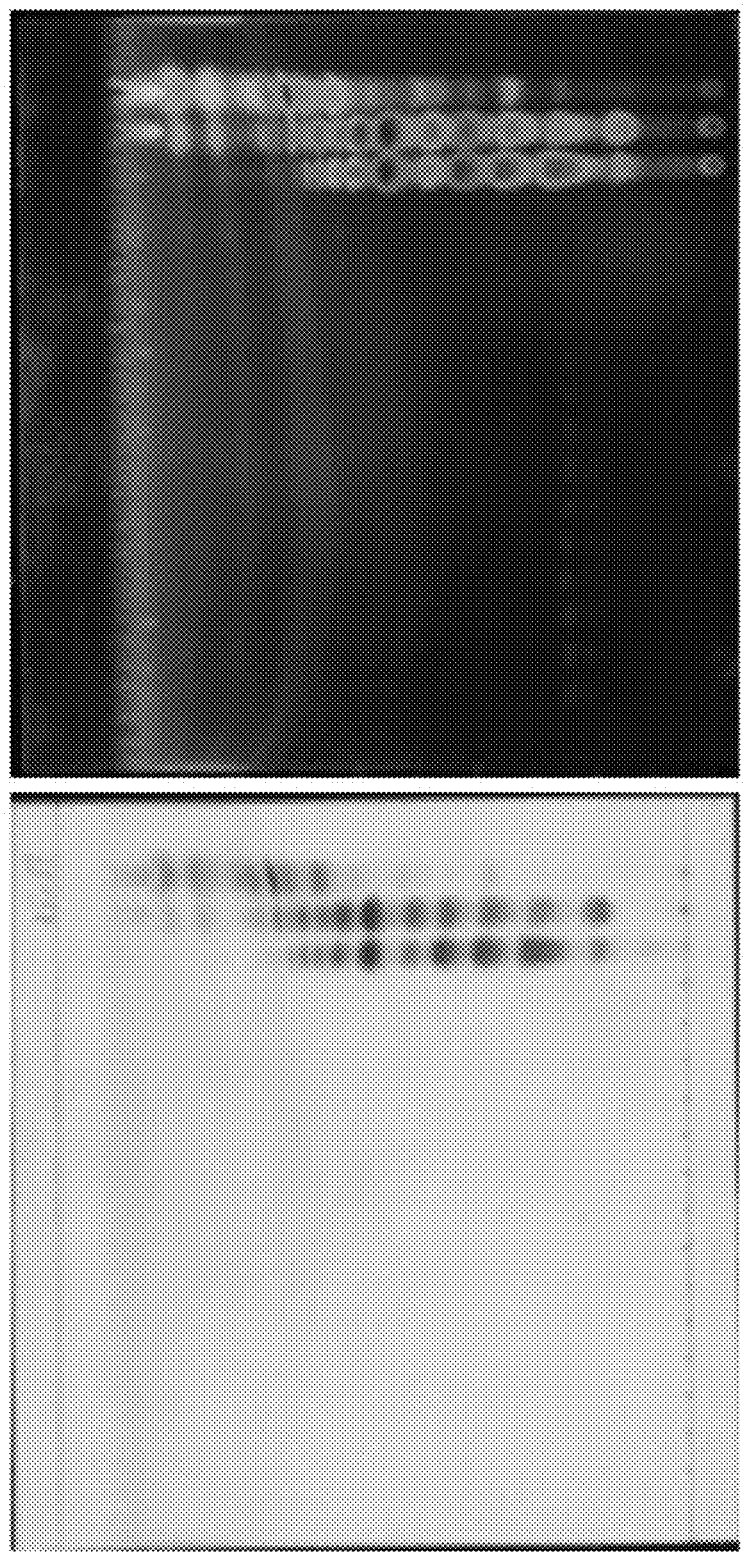

After fractionating the crude *Panax ginseng* extract comprising HSCCC separation of 4.12 g RSE extract, the elution was collected in 48 tubes. When the separation was stopped, there was still 1000 mL solution (the lower phase plus the upper phase in total) in the HSCCC column that was pushed out by high-pressure gas to make the last two fractions. As illustrated in FIG. 1, these fractions were combined to 9 fractions according to the similarity in their TLC pattern. RSE 1 was tube 1, RSE 2 was tubes 2~3, RSE 3 was tube 4, RSE 4 was tubes 5~8, RSE 5 was tubes 9~13, RSE 6 was tubes 14~28, RSE 7 was tubes 29~48, RSE 8 was the upper phase of the solution remained in the column, and RSE 9 was the lower phase. The recovery of RSE 1, 2, 3, 4, 5, 6, 7, 8 and 9 was 2.99, 46.85, 35.73, 1.52, 0.35, 0.41, 0.37, 2.15, and 3.98, respectively, and the total recovery was 94.36%.

Figure 2:
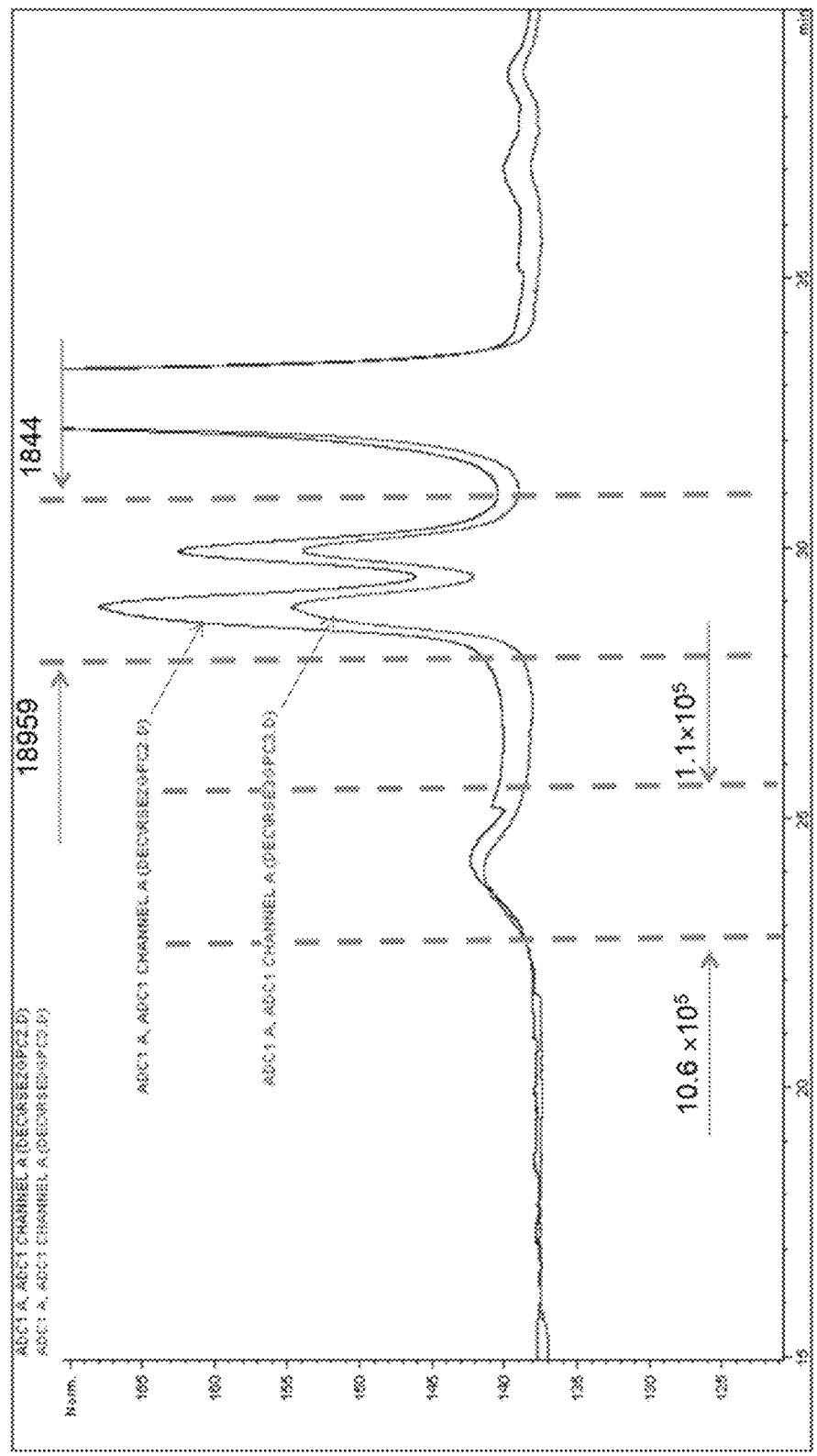
FIG. 2 shows the molecular weight distribution of two fractions from the RSE, namely the carbohydrate-enriched *Panax ginseng* extract forming RSE2 and RSE3 as determined by means of high-performance liquid chromatography (HPLC) analysis on Agilent 1100 system equipped with an ELSD detector (samples were analyzed on two TSK GMPWXL gel filtration columns in series, 7.8×300 mm×2, and eluted with 0.02 M $CH_3COONH_4$ at a flow rate of 0.6 mL/min).
Figure 3:
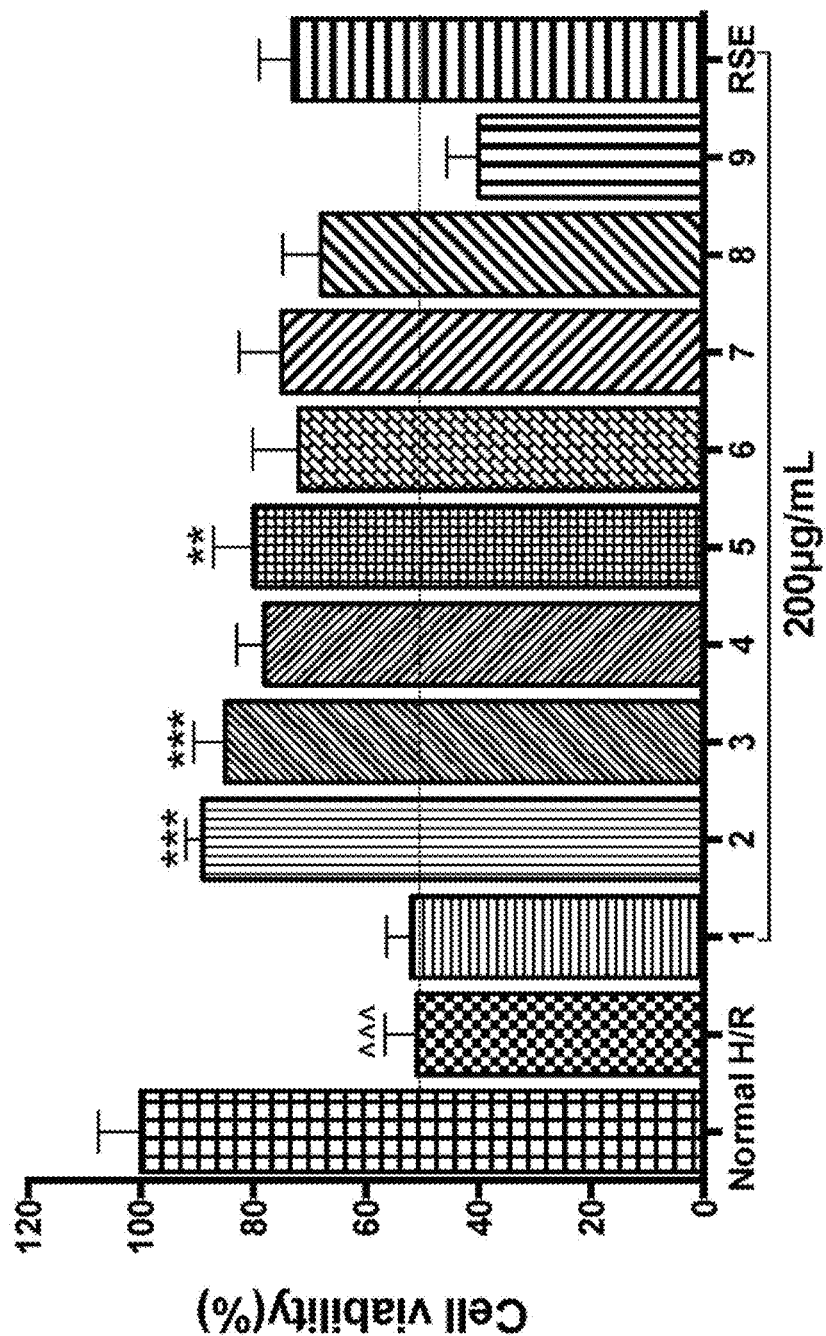
FIG. 3 illustrates the effects of different RSE fractions and RSE in H/R-induced H9c2 cells pretreated without (H/R) or with 200 µg/mL of the RSE fractions 1-9 or RSE for 24 h and then exposed to hypoxia for 3 h. The normal group (Normal) was always maintained in normoxic conditions. The cell viability was measured with MVS assay. All measurements were repeated in six wells, the results are the average of three independent experiments. All values are expressed as mean±SD. N=3. ^^^$P<0.001$ vs. normal, $P<0.01$ vs. H/R, *$P<0.001$ vs. H/R.

Among them, RSE 2 and RSE 3 were two most active fractions (FIG. 3) that exhibited identical molecular distribution pattern as revealed by HPGPC (FIG. 2). As shown in FIG. 2, in addition to the small molecules (<1800 Da), macromolecules varying from 1800 Da to $10.6 \times 10^5$ Da were also found as the major components, showing that RSE 2 and RSE 3 are the polysaccharide fractions of RSE. Further stepwise ethanol precipitation of the RSE 2/RSE 3 mixture as carbohydrate enriched *Panax ginseng* extract offered five fractions.

Figure 4:
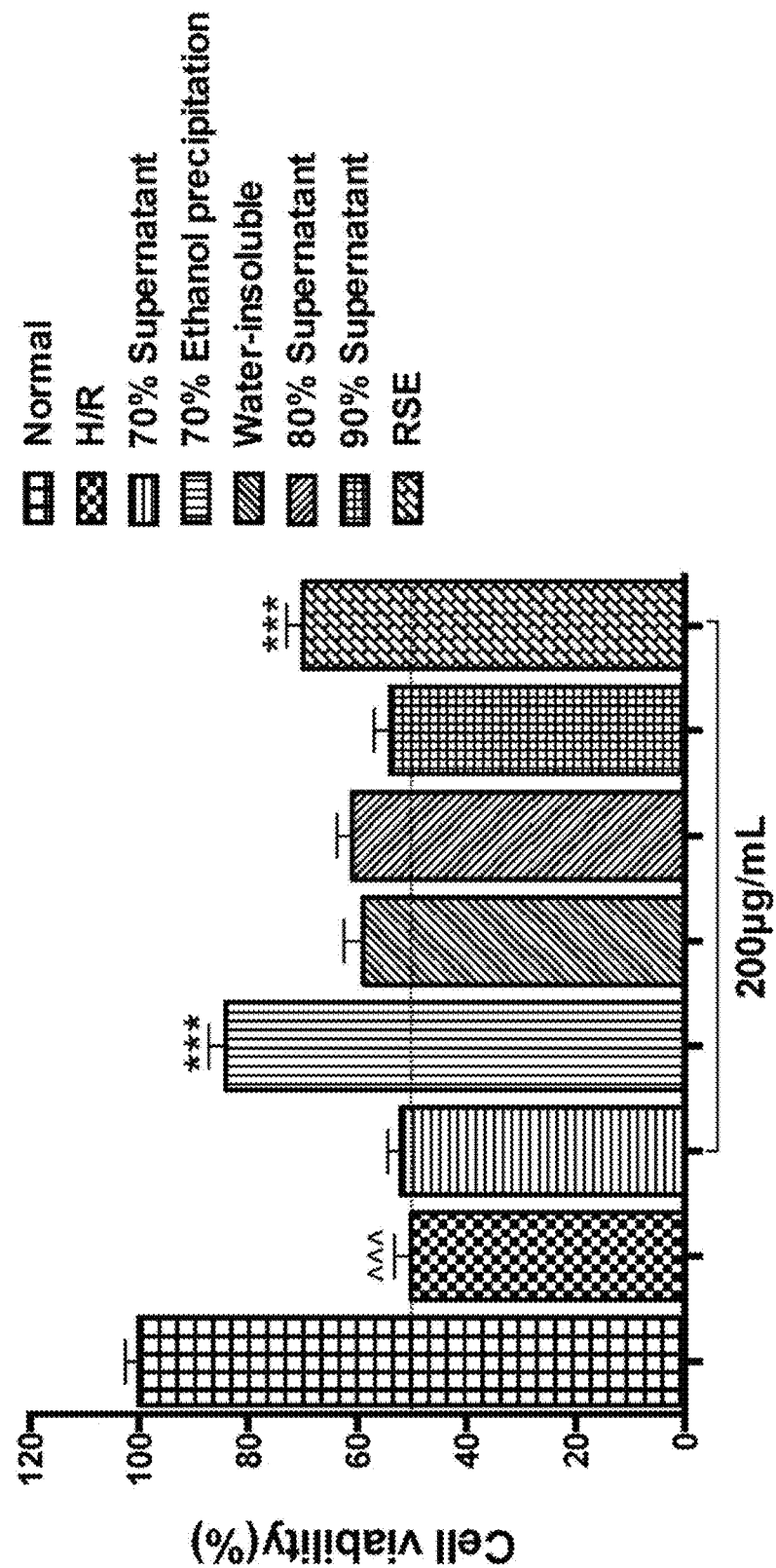
FIG. 4 illustrates the effects of carbohydrate-enriched precipitates and supernatants obtained from the carbohydrate-enriched *Panax ginseng* extract, i.e. from the fractions RSE2/3 in H/R-induced H9c2 cells pretreated without (H/R) or with 200 µg/mL of the precipitates, supernatants or RSE for 24 h and then exposed to hypoxia for 3 h. The cell viability was measured with MVS assay. The normal group (Normal) was always maintained in normoxic condition. All measurements were repeated in six wells, the results are the average of three independent experiments. All values are expressed as mean±SD. N=3. AAA P<0.001 vs. Normal, ***P<0.001 vs. H/R.
Figure 5:
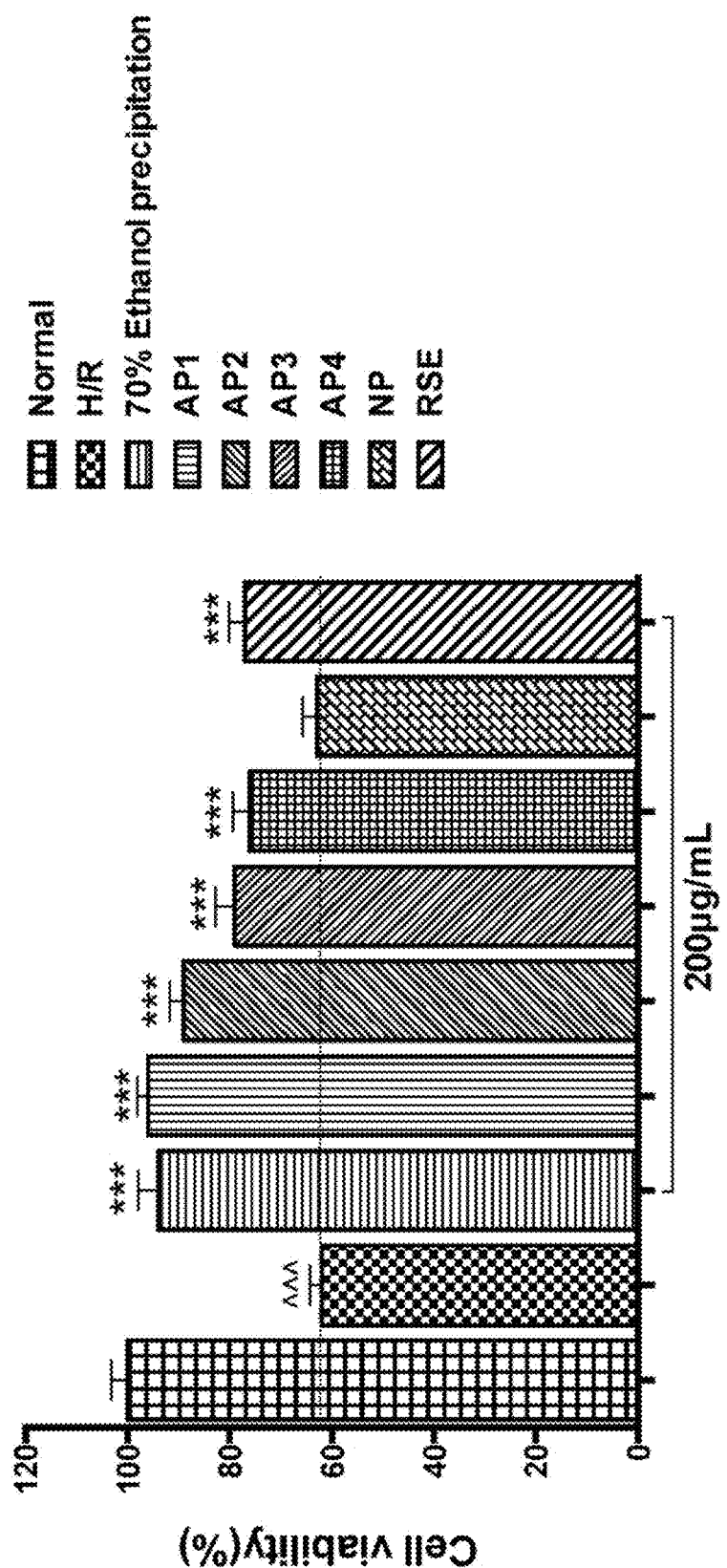
FIG. 5 illustrates the effects of carbohydrate compositions of the present invention in H/R-induced H9c2 cells pretreated without (H/R) or with 200 μg/mL of the carbohydrate compositions, a carbohydrate-enriched precipitate or RSE for 24 h and then exposed to hypoxia for 3 h. The cell viability was measured with MVS assay. The normal group (normal) was always maintained in normoxic condition. All measurements were repeated in six wells, the results are the average of three independent experiments. All values are expressed as mean±SD. N=3. ^^^P<0.001 vs. Normal, ***P<0.001 vs. H/R.

Among these five fractions, the carbohydrate enriched precipitate obtained by precipitation in 70% ethanol (recovery rate was 21.88%) exhibited the strongest activity (FIG. 4) and was further subjected onto ion-exchange column chromatography on Toyopearl DEAE 650 M. Five eluate fractions were collected, and named NP (neutral polysaccharides), AP1 (acid polysaccharides 1), AP2, AP3 and AP4. After dialysis and lyophilization, they accounted for 28.96%, 39.39%, 5.24%, 1.37%, 1.12% of total 70% ethanol precipitate fraction, respectively. The total recovery was 76.15%. Among them, the carbohydrate composition AP1 was the major fraction and showed the strongest activity (FIG. 5). AP1 accounts from 7.11% of RSE.

Figure 6A:
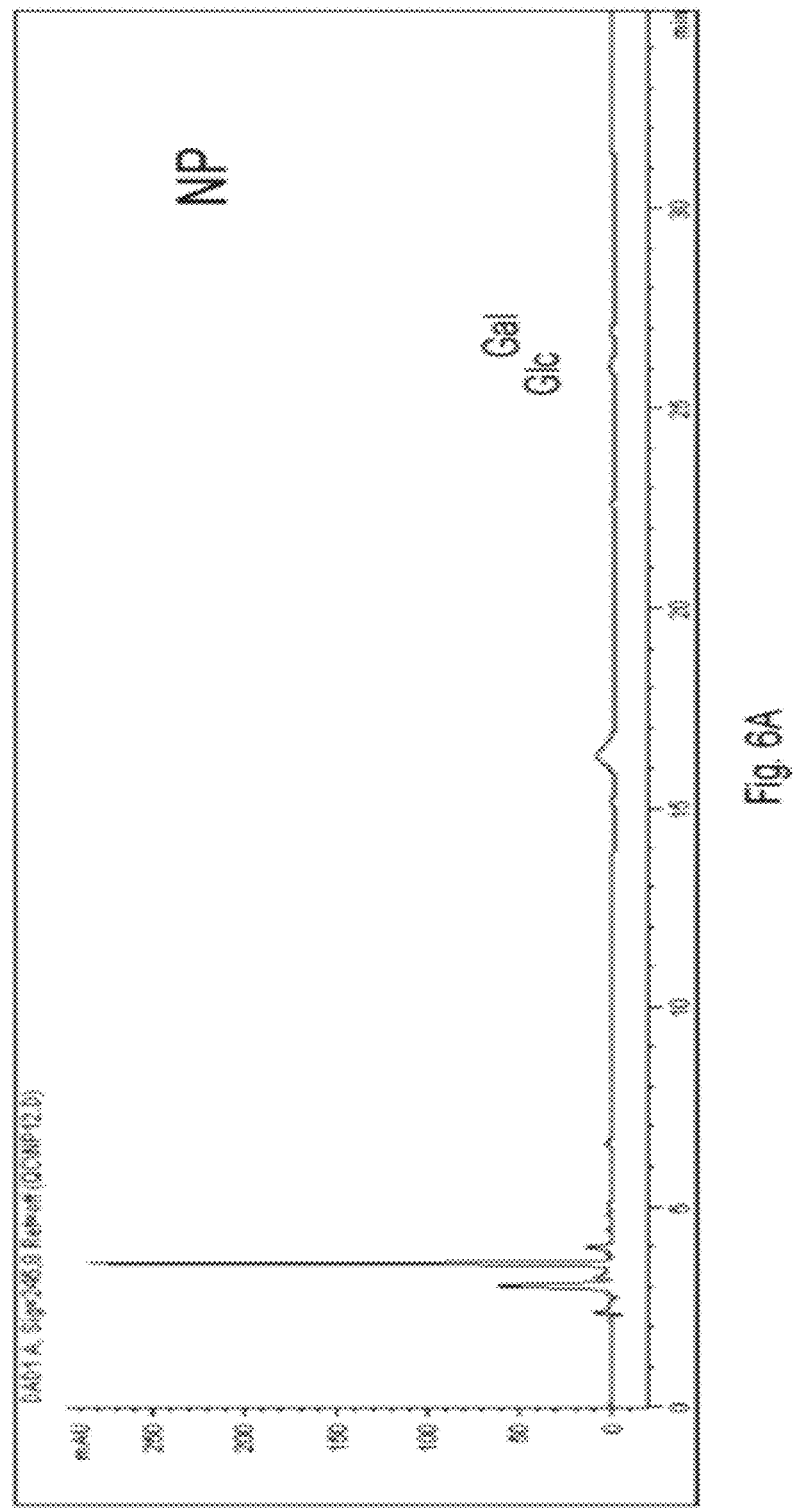

The total sugar content of the carbohydrate composition AP1 was determined to be 90.28% using Glc as the reference. Its uronic acid content was determined to be 17.93% using Gal A as the standard. The protein content was determined to be 9.85%. The apparent molecular weight of AP1 was estimated to be $3.8 \times 10^4$, with reference to dextran. As shown in FIG. 6, sugar composition analysis revealed that AP1 was mainly composed of glucose (Glc, 76.31%), galactose (Gal, 12.70%) with small amount of galacturonic acid (Gal A, 5.64%), arabinose (Ara, 3.72%), and glucuronic acid (Glc A, 1.64%). Based on these results, AP1 was characterized to be an acidic heteroglycan.

Figure 7:
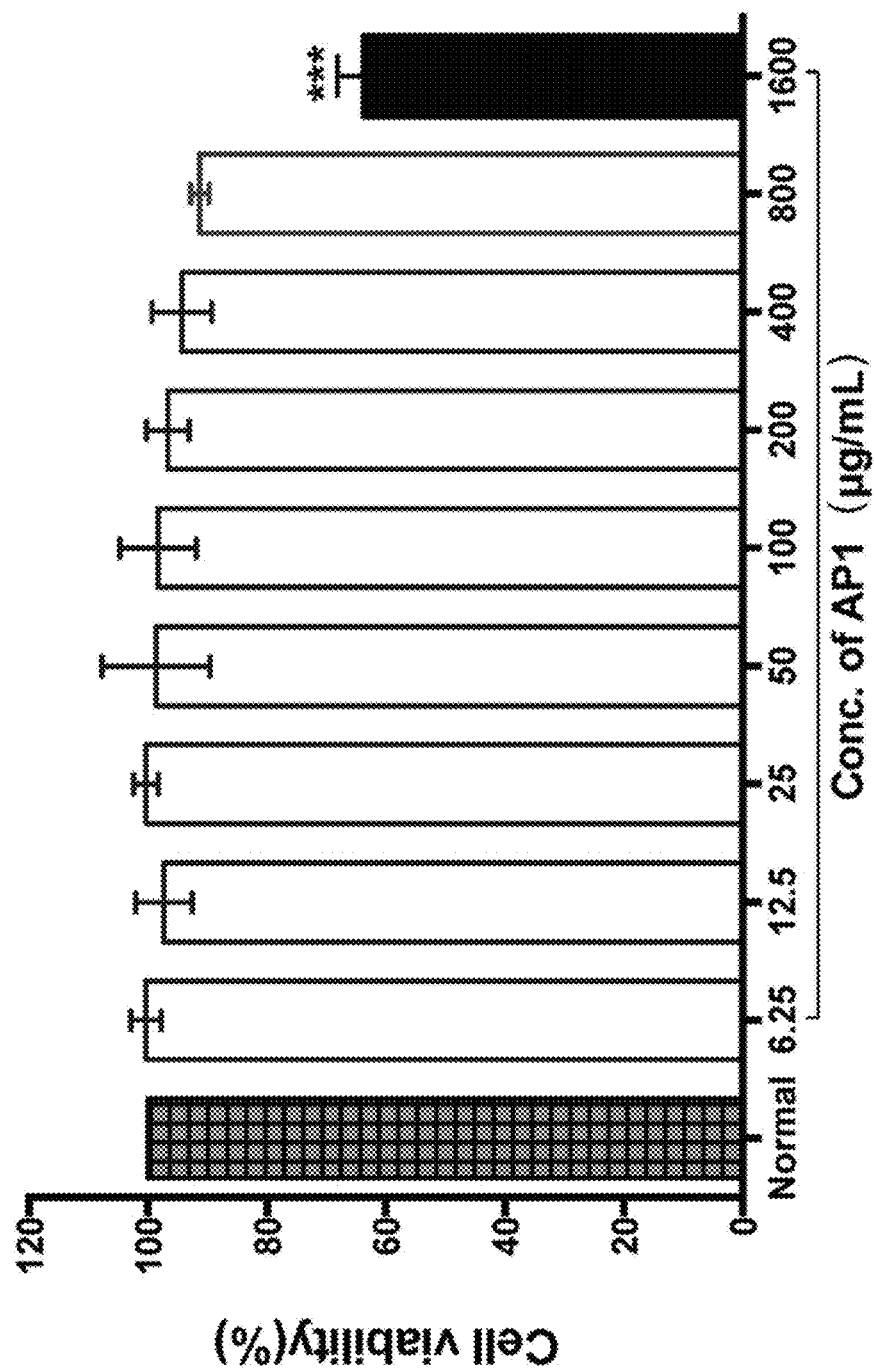
FIG. 7 refers to the cytotoxicity of the carbohydrate composition AP1 in H9c2 cells under normoxic conditions. Cellular viability was determined by MVS assay. All measurements were repeated in six wells, the results are the average of three independent experiments. All values are expressed as mean±SD. N=3. ***P<0.001 vs. Normal.

As presented in FIG. 7, treatment with the carbohydrate composition AP1 at concentrations of 6.25 μg/mL to 800 μg/mL resulted in no significant alterations in H9c2 cell growth. However, treatment with even higher concentrations (>800 μg/mL) of AP1 resulted in a significant loss of cell viability. Therefore, the optimal and nontoxic concentrations of AP1 were proposed to be 6.25 to 800 μg/mL in H9c2 cardiomyocytes.

Figure 8E:
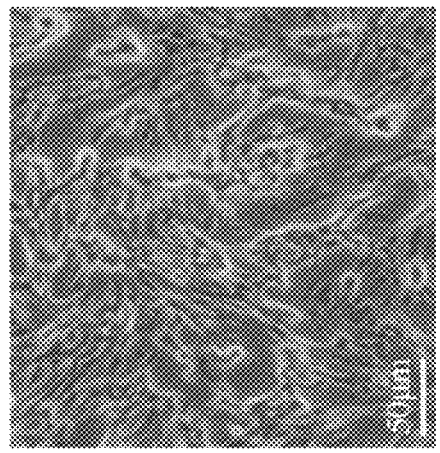
FIG. 8A through 8E show the cell morphology of H9c2 cell pretreated with the carbohydrate composition AP1 in the H/R model.
Figure 8C:
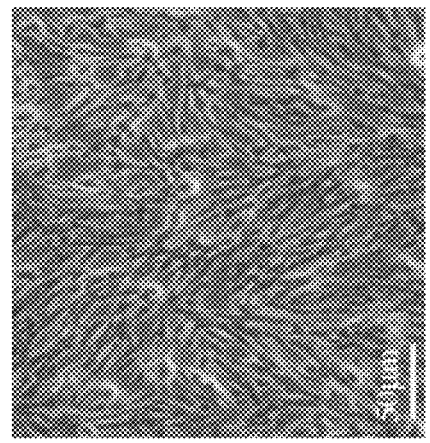
Figure 8D:
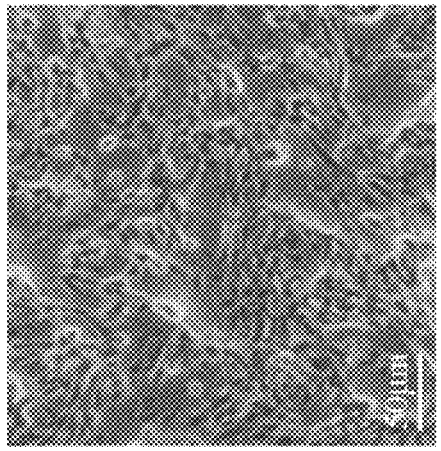
Figure 8A:
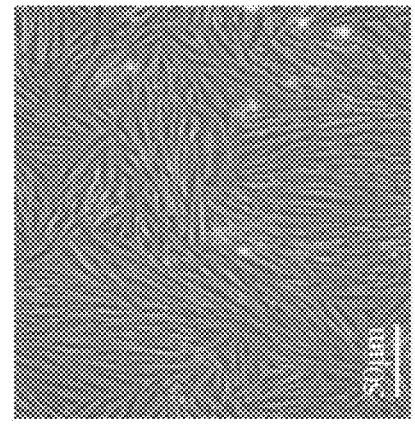
Figure 8B:
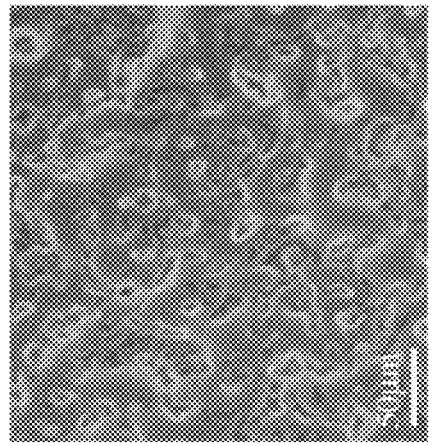
Figure 9:
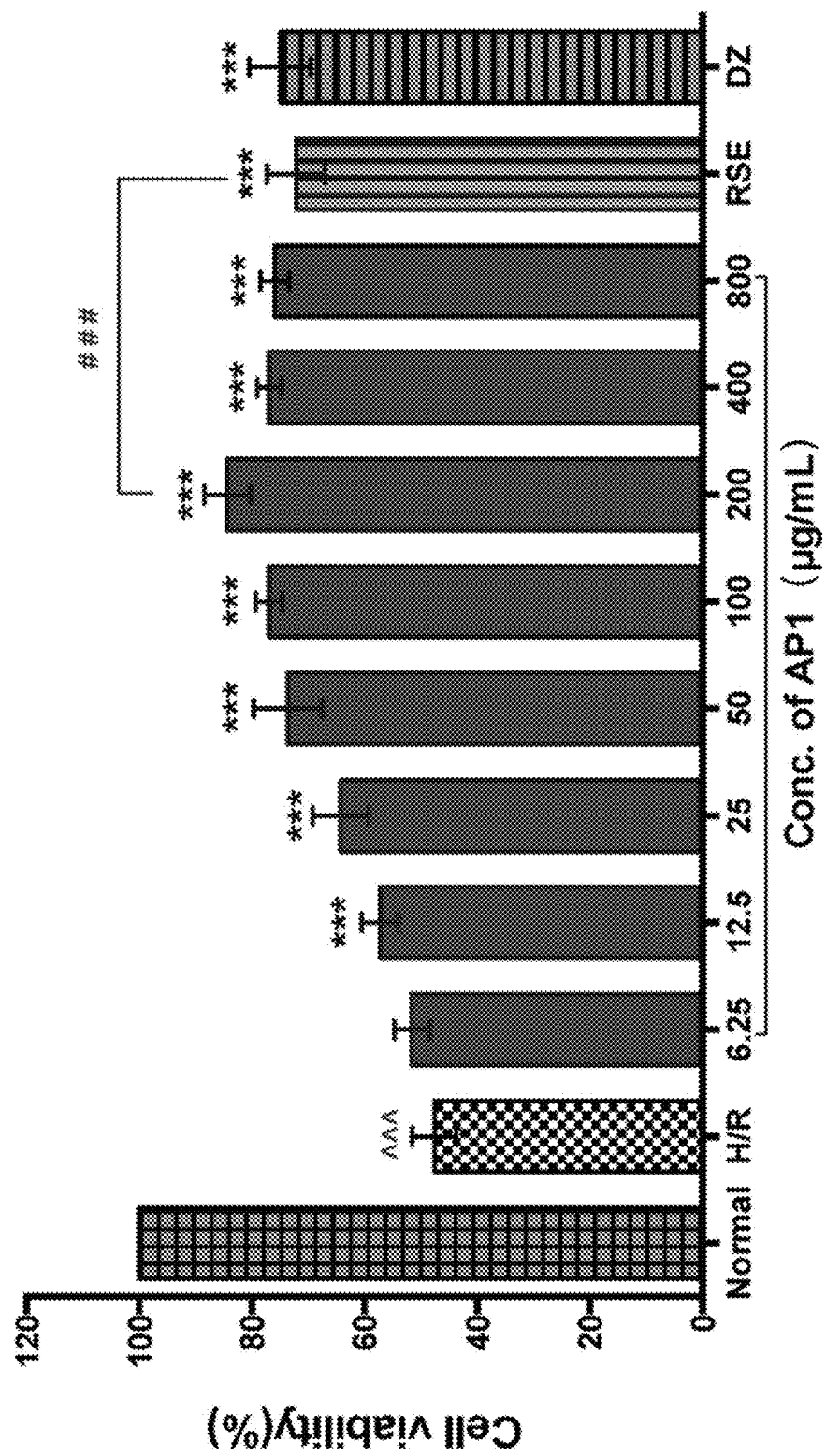
FIG. 9 illustrates the protective effects of the carbohydrate composition AP1 against H/R injury in H9c2 cells. H9c2 cells were pretreated without (H/R) or with 6.25 μg/mL to 800 μg/mL of AP1 or 200 μg/mL of RSE or 100 μM of DZ for 1 h and then exposed to hypoxia for 3 h followed by reoxygenation for 4 h and then the cell viability was measured with a MVS assay. The normal group (Normal) was always maintained in normoxic conditions. All measurements were repeated in three wells, the results are the average of three independent experiments. All values are expressed as mean±SD. N=3. ^^^P<0.001 vs. Normal, *P<0.05 vs. H/R, P<0.01 vs. H/R, *P<0.001 vs. H/R, ####P<0.001 vs. RSE.

The protective effect of the carbohydrate composition AP1 against H/R-induced injury in H9c2 cells wax evaluated by morphological change (FIG. 8A to 8E) and MVS assay (FIG. 9). As indicated in FIG. 8A, normal H9c2 cells adhered to the plate uniformly, with a filamentous shape, which was consistent with other reports (Sardao, V. A. et al., Cell Biol Toxicol 25, 227-243, 2009). On the contrary, when exposed to hypoxia for 3 h and reoxygenated for 4 h, H9c2 cells exhibited morphological variations, i.e. becoming round or irregular in shape, indicating the cytotoxic capacity of H/R injury (FIG. 8B). However, the cell status appeared much better in the cells pretreated with different dosages of AP1 (12.5 to 200 μg/mL). Moreover, when RSE and AP1 intervenes with the H/R damage cells under the same concentration (200 μg/mL), by morphological change, it can be seen that the morphology of cells pretreated with AP1 is significantly better than that with RSE (FIG. 8C vs. FIG. 8D). Meanwhile, in the positive group, pretreatment with diazoxide (DZ), a mitochondria potassium channel opener (Janjua, M. B. et al., Journal of the American College of Surgeons 219, 803-813, 2014) and proven to exert protective effects against I/R injury in hearts and cardiomyocytes (Henn, M. C. et al., Journal of the American College of Surgeons 221, 319-325, 2015) at 100 μM also brought a significant protection in H/R induced cell death as did by AP1 and RSE (FIG. 8E). This phenomenon has been further verified through MVS experiment (FIG. 9). It can be seen that the influence of AP1 and RSE under the same concentrations on the cell activity has significantly statistical significance (###P<0.001 vs. RSE); the protection of AP1 to H9c2 cell can be remarkably increased by about 20% as compared to RSE (FIG. 9).

Figure 10A:
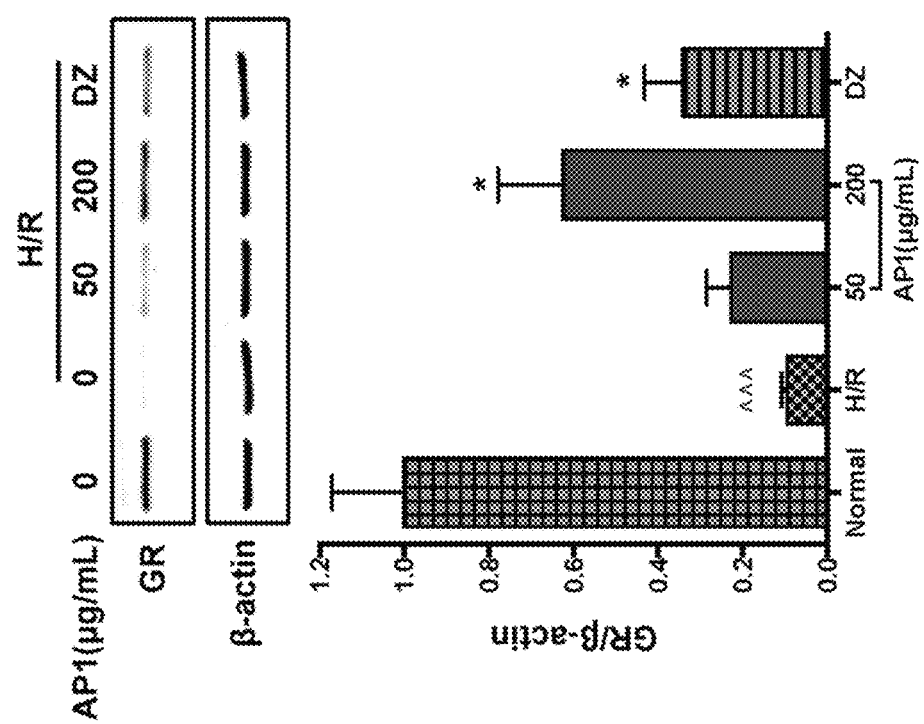
FIG. 10A through 10I illustrate the effects of treatment with the carbohydrate composition AP1 on activation and expression of the steroid hormone receptors GR and ER, the RISK pathway, eNOS and iNOS after H/R injury with Western blotting analysis. H9c2 cells were pretreated without (H/R) or with various concentrations of AP1 (50 μg/mL and 200 μg/mL) or positive control (DZ, 100 μM) for 1 h, and then exposed to hypoxia for 3 h followed by reoxygenation for another 4 h. The normal group (Normal) was always maintained in normoxic condition. The cells were collected for Western blotting analysis. The blot was probed with antibodies specific to GR, ER, Erk1/2 or phosphor-Erk1/2, P38 or phospho-P38, JNK or phospho-JNK, PI3K or phospho-PI3K, Akt or phospho-Akt, eNOS or phospho-eNOS and iNOS and read by densitometric analysis. Normalization of Western blot was ensured by β-actin. Identical results were obtained in three independent experiments. All values are expressed as mean±SD. ^^^P<0.001 vs. Normal, *P<0.05 vs. H/R, P<0.01 vs. H/R, *P<0.001 vs. H/R.
Figure 10B:
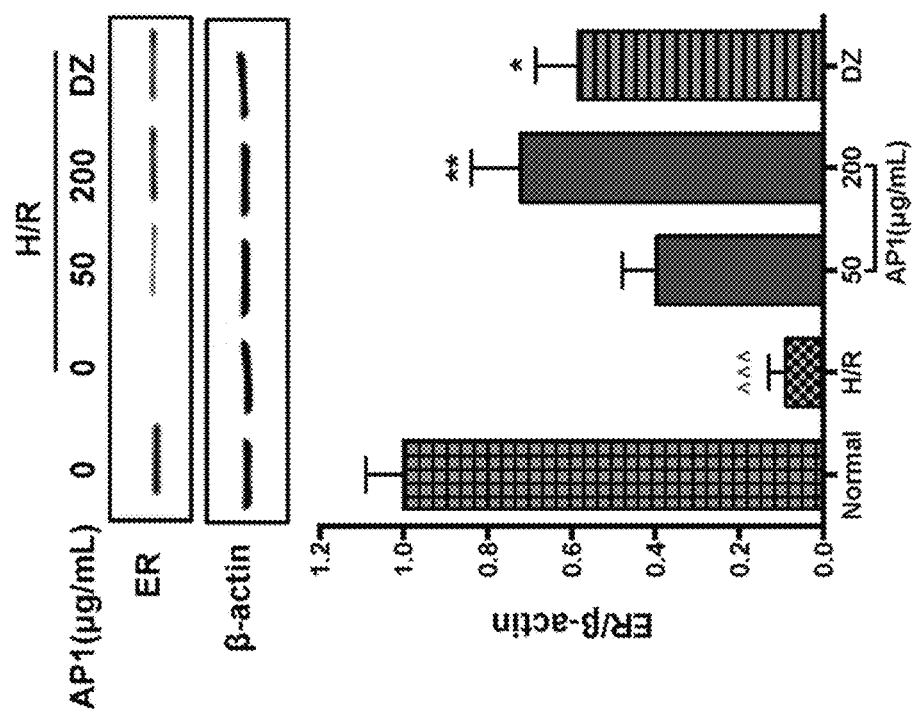
Figure 10C:
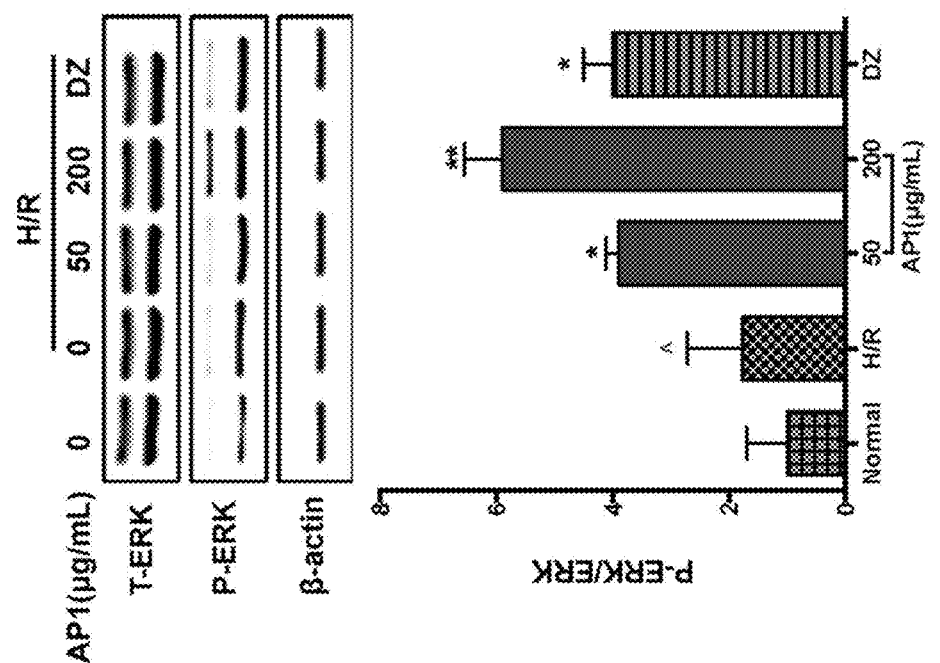
Figure 10D:
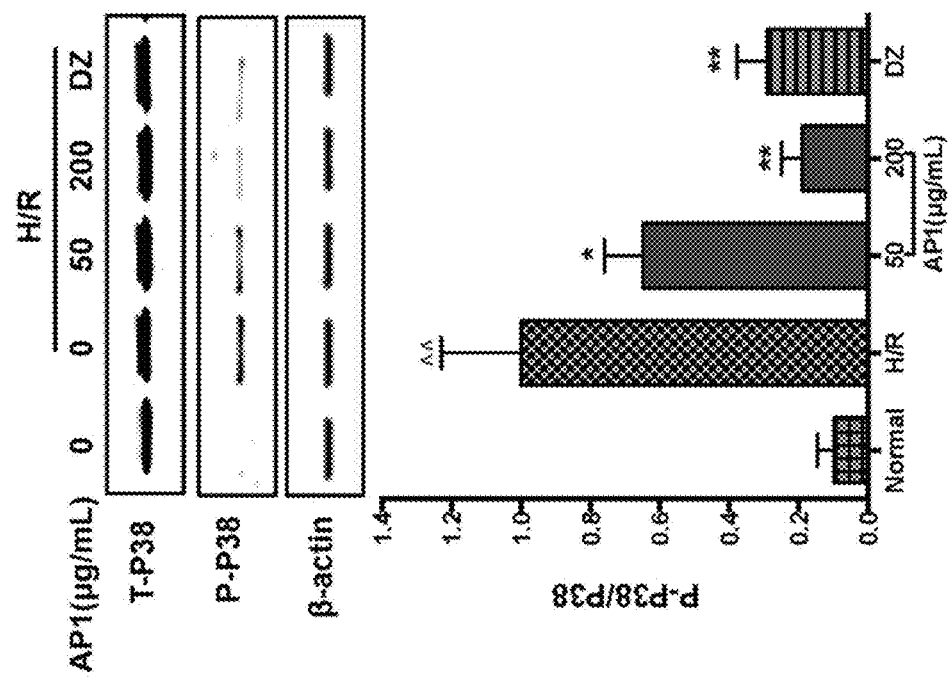
Figure 10E:
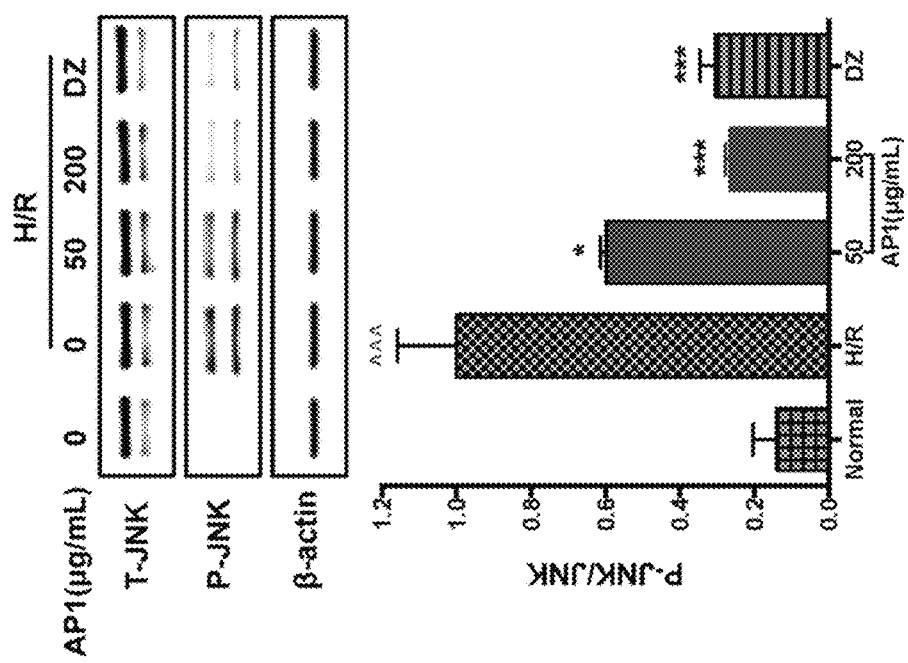
Figure 10F:
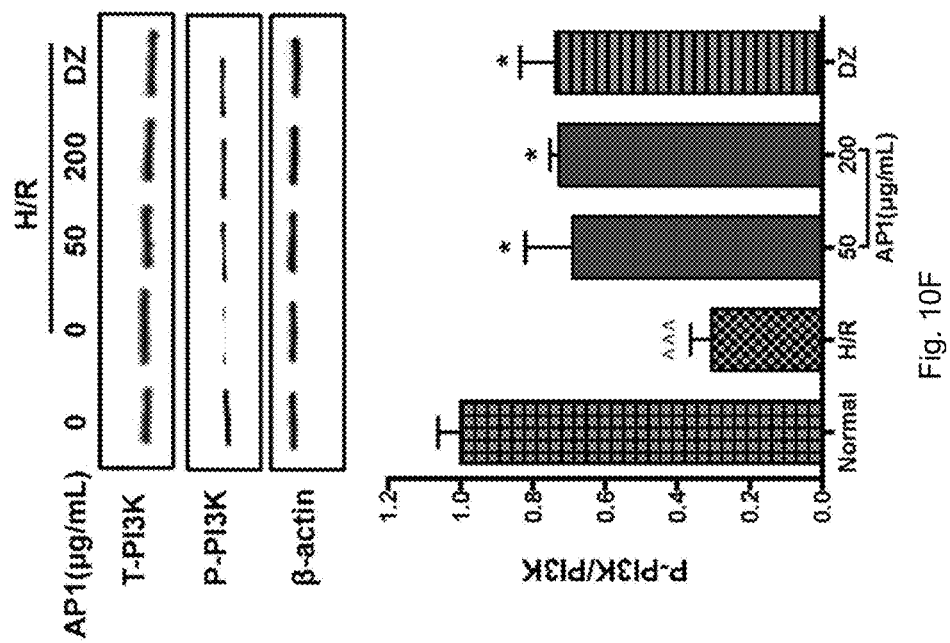
Figure 10G:
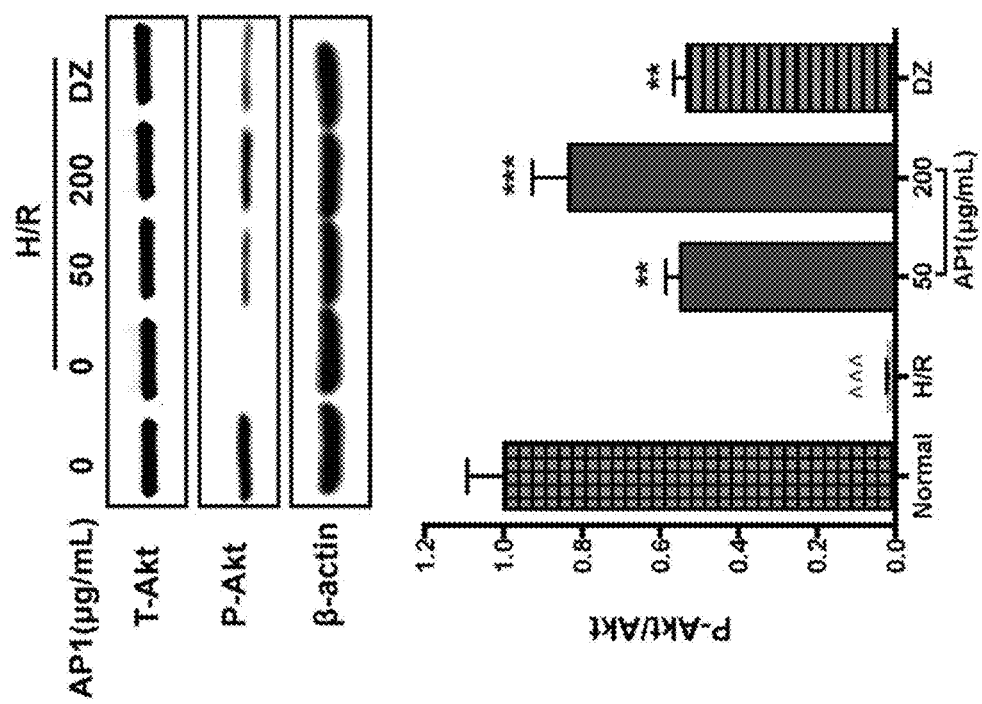
Figure 10H:
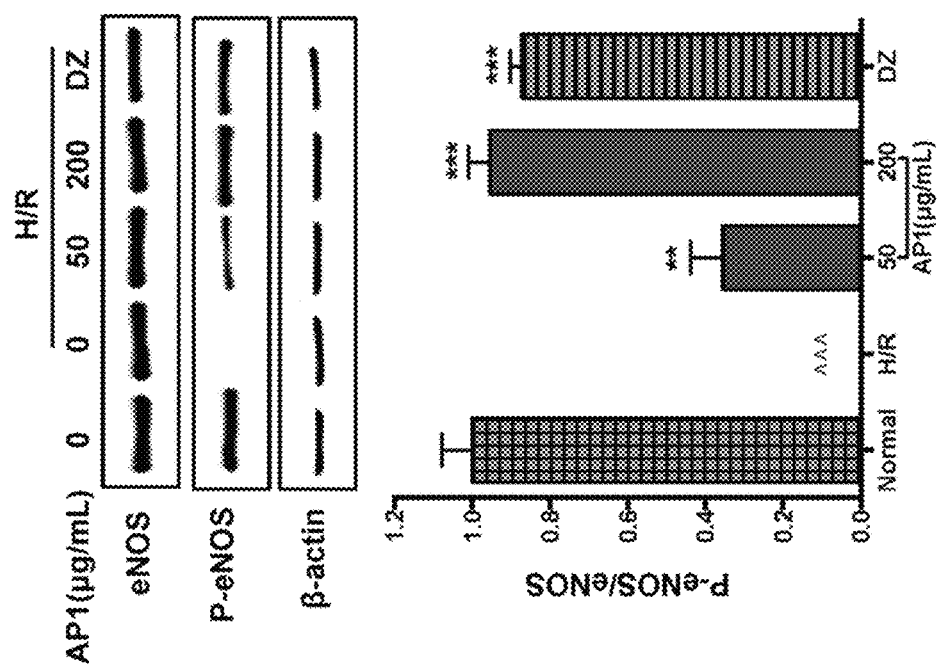
Figure 10I:
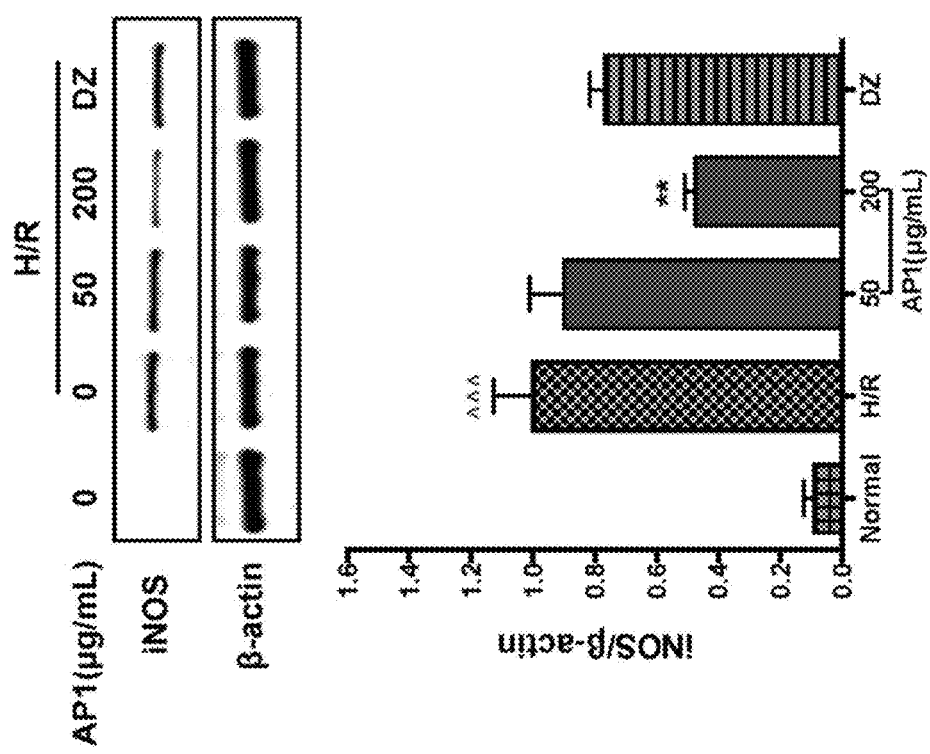

Evidences indicate that *ginseng* could exert its cardio-protective effect by activating RISK pathway, which is the term given to a group of pro-survival protein kinases (including PI3K/Akt, Erk1/2, and eNOS) that confer powerful cardio-protection (Zhou, H. et al., J Ethnopharmacol 135, 287-298, 2011). It has been examined whether the cardio-protective effect of AP1 is related to the activation of these pathways. As shown in FIG. 10, H/R led to significant suppression of GR and ER (FIGS. 10A and 10B). Although H/R had no influence on the expression of Erk1/2, PI3K/Akt and eNOS, it significantly inhibited the phosphorylation of Erk1/2, PI3K/Akt and eNOS (FIGS. 10C, F, G and H). H/R also induced significant increase of iNOS expression (FIG. 10I). AP1 pretreatment increased the protein level of GR, ER and the phosphorylated expression of PI3K, Akt, Erk1/2 and eNOS, and suppressed the expression of iNOS in a dose dependent manner. The effect of AP1 on these proteins is even better than the positive control diazoxide. All these results indicate that AP1 has a great cardio-protective potential possibly through regulating RISK pathway.

Figure 11:
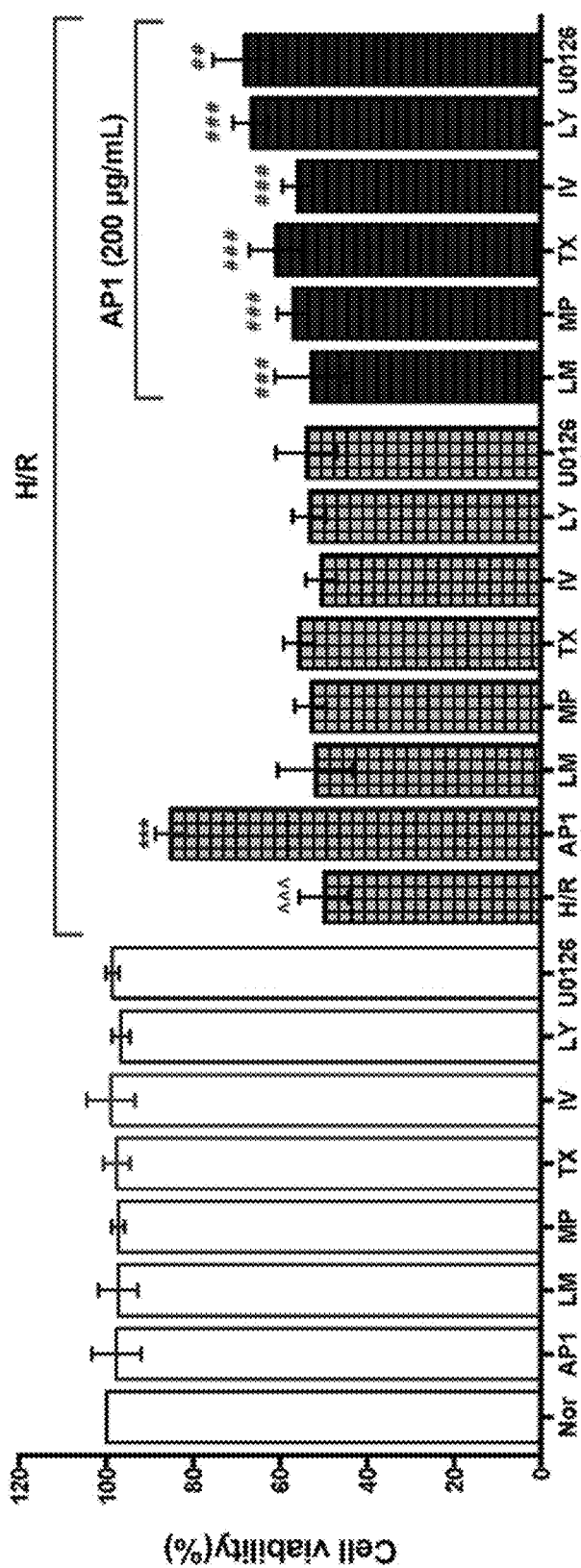
FIG. 11 shows the impact of survival pathway inhibitors on carbohydrate composition AP1-induced cardio-protection in H/R-induced H9c2 cells. H9c2 cells were pre-cultured in the presence or absence of survival pathway inhibitors, including mifepristone (MP, 100 μM), tamoxifen (TX, 100 μM), L-NAME (LM, 10 μmol/L), LY294002 (LY, 40 μM), Akt inhibitor IV (IV, 10 μM), U0126 (40 μM) with or without 200 μg/mL AP1 for 1 h, and then exposed further to H/R injury. The normal group (NOR) was always maintained in normoxic condition. Cell death was assessed by MVS assay. All measurements were repeated in six wells, the results are the average of three independent experiments. All values are expressed as mean±SD. ^^^P<0.001 vs. NOR, ***P<0.001 vs. H/R, ##P<0.01 vs. AP1 under H/R, ####P<0.001 vs. AP1 under H/R.
Figure 12:
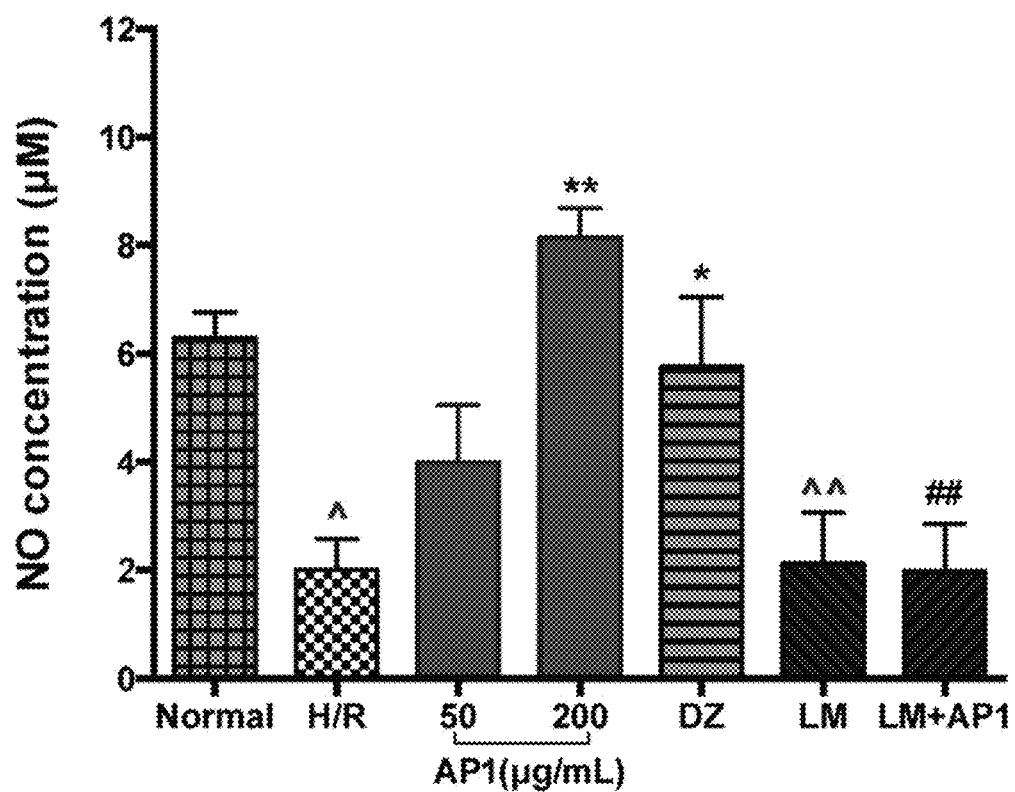
FIG. 12 illustrates the effect of carbohydrate composition AP1 on NO production. H9c2 cells were pretreated without (H/R) or with 50 μg/mL and 200 μg/mL of AP1 or 100 μM of DZ or 10 μmol/L of L-NAME (LM) or 10 μmol/L of L-NAME and 200 μg/mL of AP1 (LM+AP1) for 1 h and then exposed to hypoxia for 3 h followed by reoxygenation for 4 h. The normal group (Normal) was always maintained in normoxic condition. The changes of NO levels in culture medium of H9c2 cells following H/R injury were determined by Griess reagent. The results are the average of three independent experiments. All values are expressed as mean±SD. ^P<0.05 vs. Normal, **P<0.01 vs. H/R, ####P<0.001 vs. AP1 (200 μg/mL).
Figure 13A:
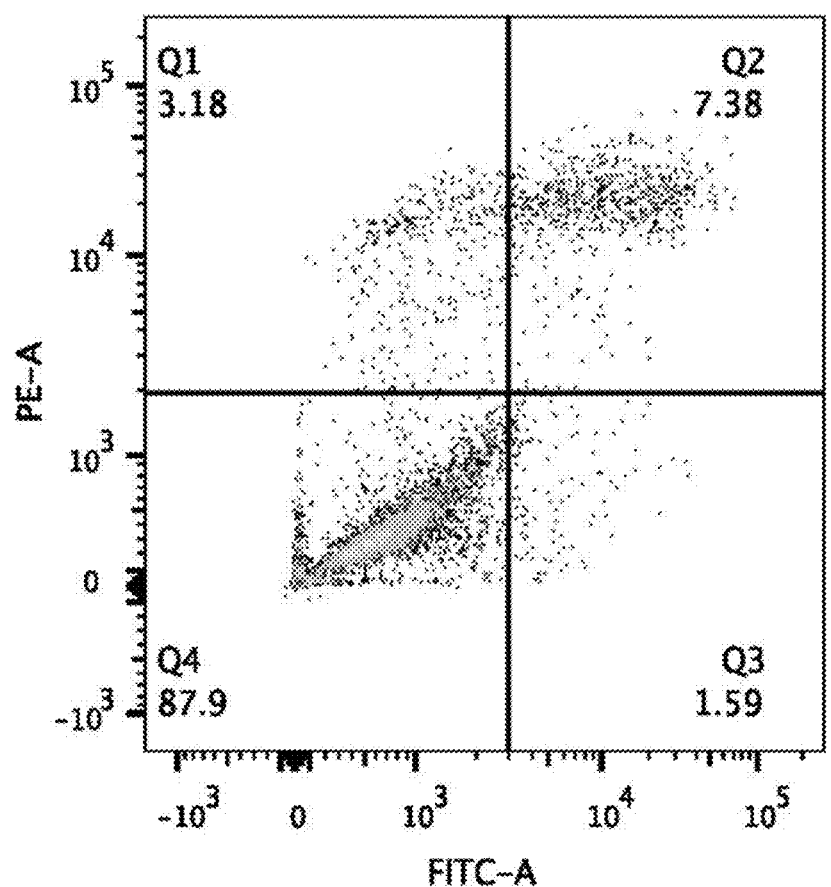
FIG. 13A through 13F show the effects of carbohydrate composition AP1 on apoptosis rate revealed by flow cytometry. H9c2 cells were pretreated without (H/R) or various concentrations of AP1 (50 μg/mL and 200 μg/mL) or positive control (DZ, 100 μM) for 1 h, and then exposed to hypoxia for 3 h followed by reoxygenation for another 4 h. The normal group (Normal) was always maintained in normoxic condition. The cells were then stained with Annexin V-FITC and PI for apoptosis analysis by flow cytometry. Cells in the lower-left quadrant (Q3), unstained for both Annexin V-FITC and PI, are defined as viable cells. Cells in the lower-right quadrant (Q4), stained for Annexin V-FITC but negative for PI, are defined as early-medium apoptotic cells. Cells in the upper-right quadrant (Q2), positive for both Annexin V-FITC and PI, are defined as late apoptotic and necrotic populations. The results are the average of three independent experiments. All values are expressed as mean±SD. $^{\wedge\wedge\wedge}$P<0.001 vs. Normal, *P<0.05 vs. H/R, P<0.01 vs. H/R, *P<0.001 vs. H/R.
Figure 13B:
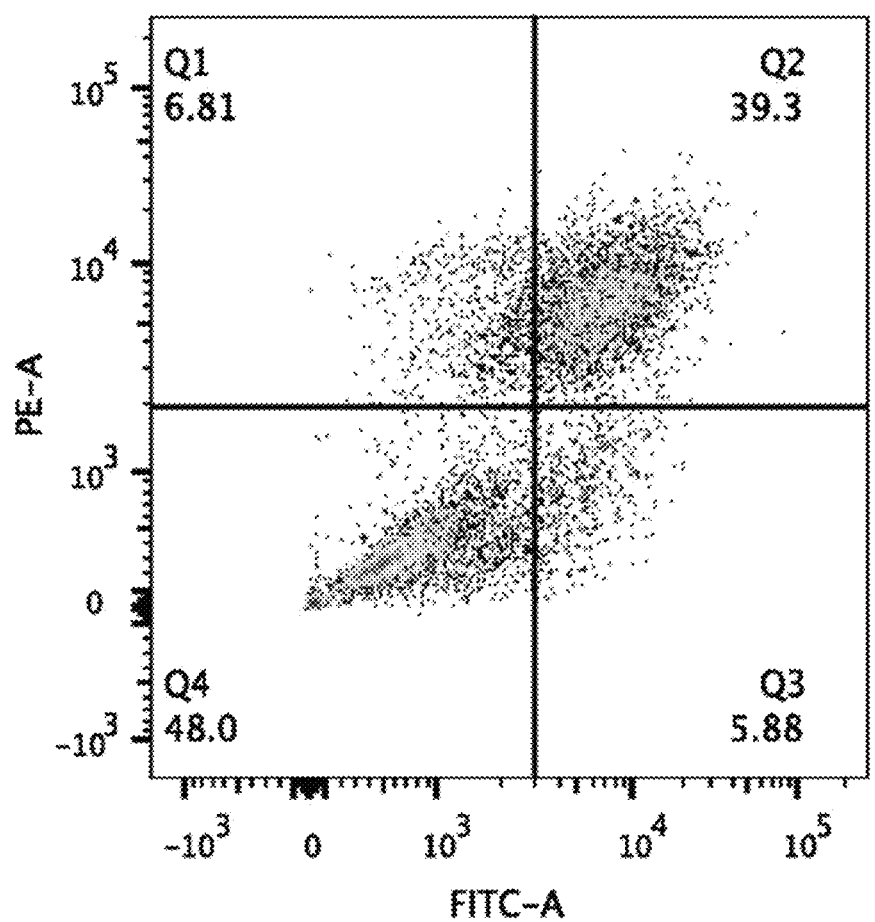
Figure 13C:
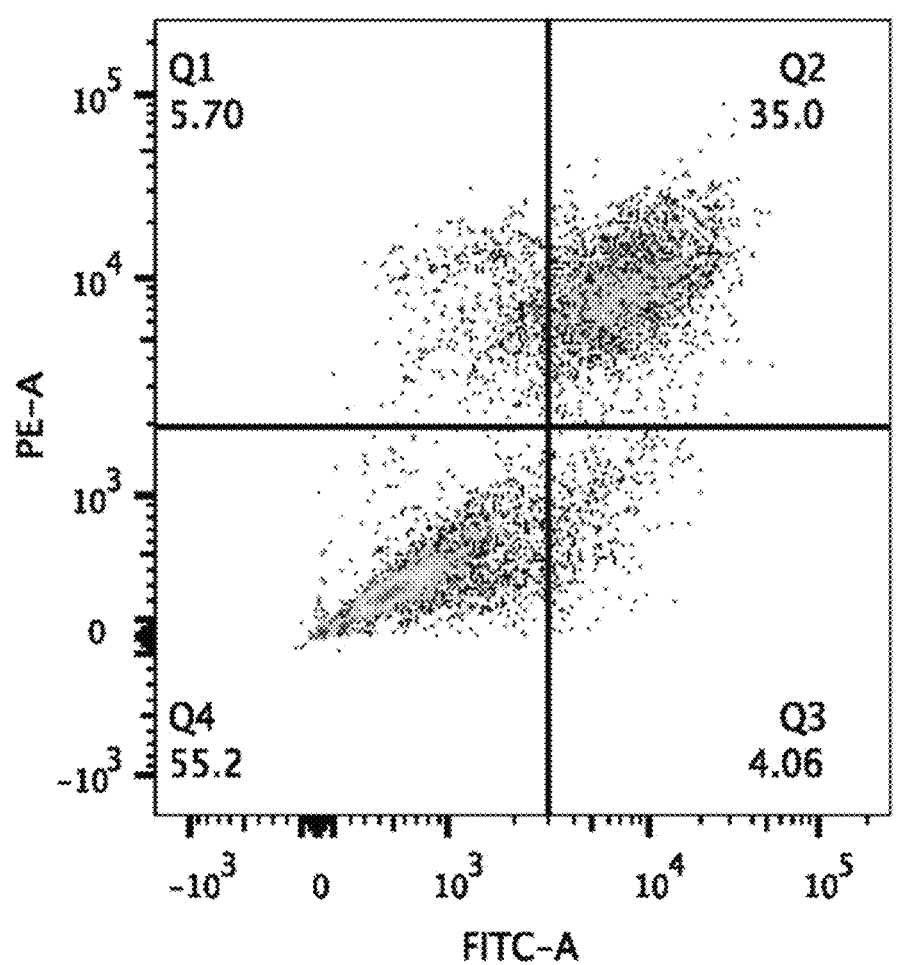
Figure 13D:
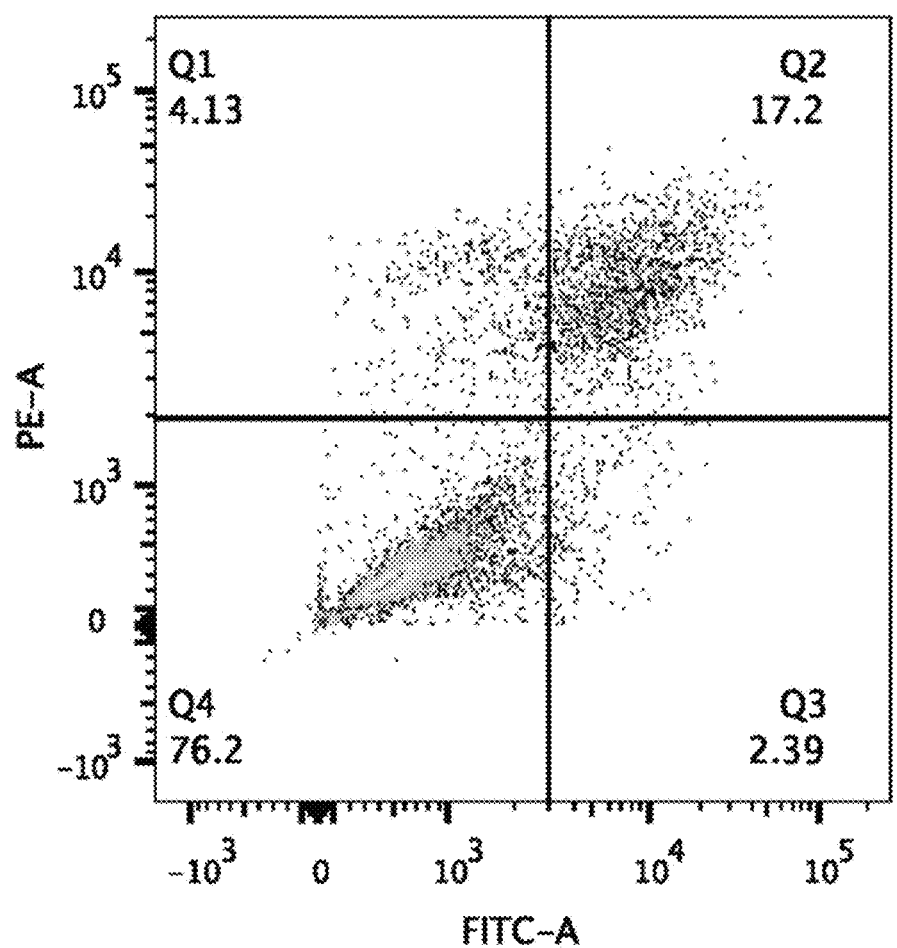
Figure 13E:
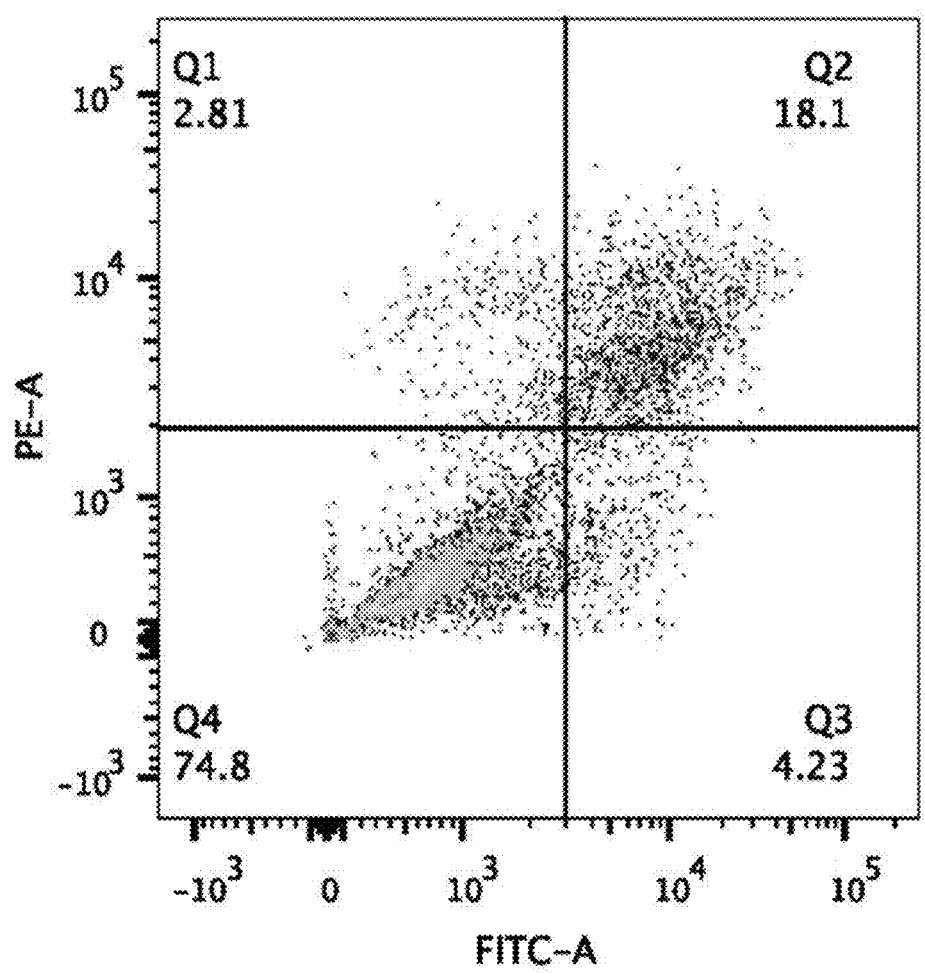
Figure 13F:
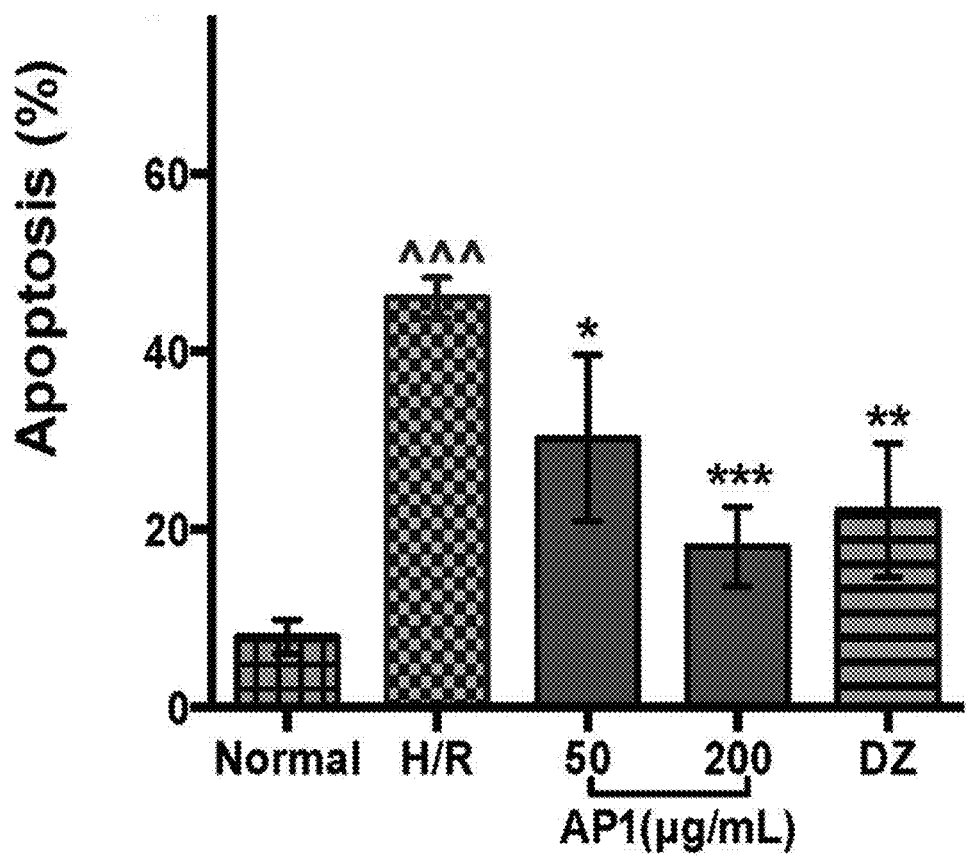

To further confirm whether the above signaling pathways were involved in the pre-survival function of AP1, H9c2 cells were pre-incubated with the GR inhibitor mifepristone, the ER inhibitor tamoxifen, the PI3K inhibitor LY294002, the Akt inhibitor IV, the Erk1/2 inhibitor U0126 and the NOS inhibitor L-NAME and exposed to H/R injury in the absence or presence of AP1. As a result, these inhibitors abolished the protective effects of AP1 on H/R-induced cell death, showing that these proteins play an important role in the cardio-protective effects of AP1 in H9c2 cells (FIG. 11).

The suppressed production of nitric oxide (NO) is thought to be a cause of ischemia and reperfusion injury of the heart. But findings of the salutary effects of NO enhancement on such injury have been conflicting. It has been evaluated whether NO enhancement would attenuate ischemia/reperfusion injury. To determine whether protective effects of the carbohydrate composition AP1 against H/R-induced cell death are via an NO-mediated mechanism, the amount of NO produced was measured. The results showed pretreatment of AP1 at 200 μg/mL in H9c2 cells that underwent a H/R process resulted in a remarkable elevation of the amount of NO by 61.1% (compared with the H/R group, P<0.001). Furthermore, the H/R induced NO production was significantly abolished by specific eNOS inhibitor, L-NAME (10 μmol/L).

Apoptosis is the major mechanism of cell death immediately following a short period of ischemia with ensuring reperfusion. The cellular apoptosis was assessed by flow cytometry (FIG. 13A to 13F). Annexin V/PI double staining demonstrated significant apoptotic increase in the H/R group indicating an apoptotic cell accumulation of 46.0%±1.2%, while AP1 at the concentration of 50 and 200 μg/mL as well as the positive control DZ significantly attenuated H/R induced apoptosis (30.3%±4.7%, 18.1%±2.2% and 22.2±3.8%).

Figure 14A:
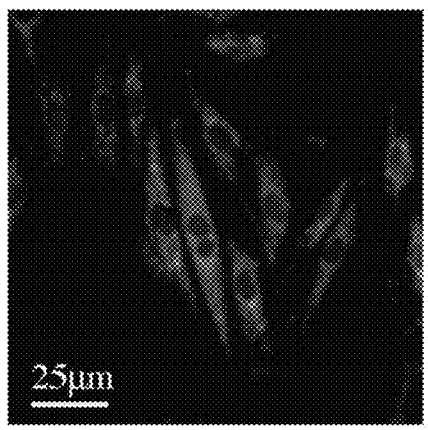
FIG. 14A through 14F show the effects of AP1 on the mitochondrial membrane potential. H9c2 cells were pretreated with various concentrations of AP1 (50 µg/mL and 200 µg/mL) or positive control (DZ, 100 µM) for 1 h, and then exposed to hypoxia for 3 h followed by reoxygenation for another 4 h. The normal group (Normal) was always maintained in normoxic condition. Mitochondrial membrane potential was measured by rhodamine 123 (Rh 123). The results are the average of three independent experiments. All values are expressed as mean±SD. $^{\wedge\wedge\wedge}$P<0.001 vs. Normal, *P<0.05 vs. H/R, **P<0.01 vs. H/R.
Figure 14D:
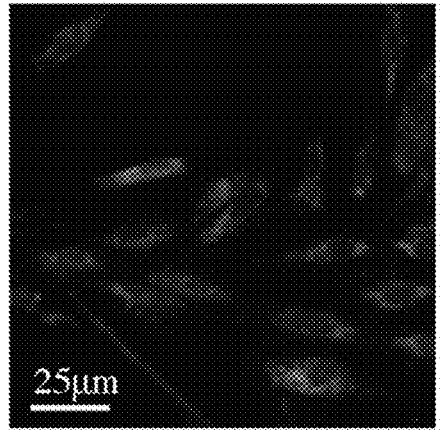
Figure 14B:
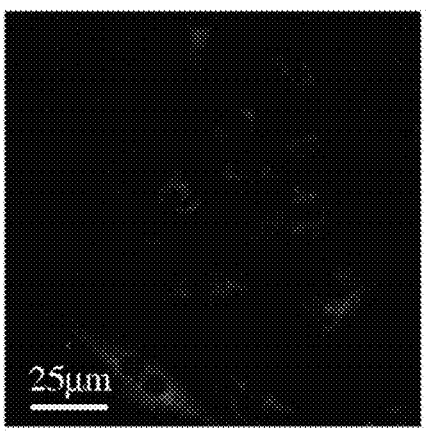
Figure 14E:
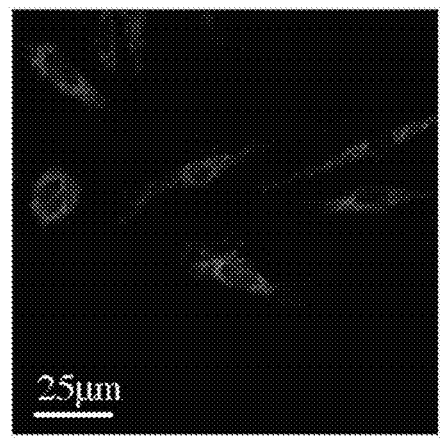
Figure 14C:
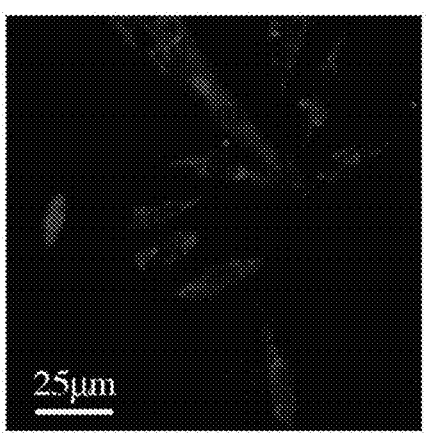
Figure 14F:
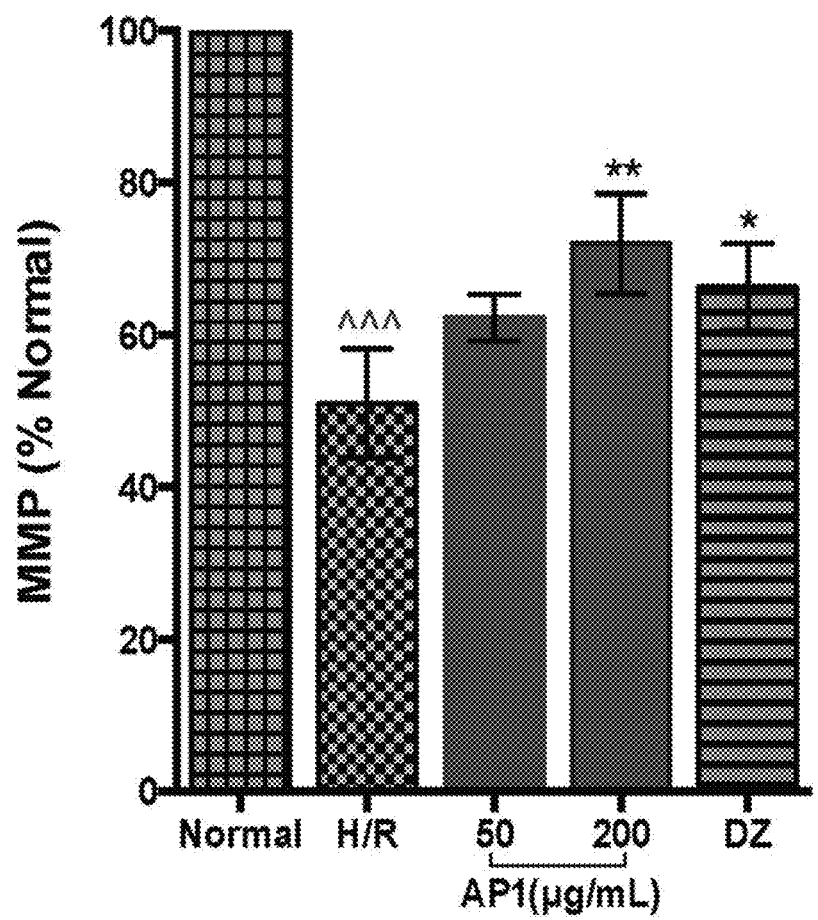

To determine the association of cell apoptosis with mPTP, the change of mitochondrial membrane potential has been evaluated as an indicator of mPTP opening. Exposure of cardiomyocytes with 3 h hypoxia followed by 4 h reperfusion resulted in a decrease in Rh123 fluorescence as detected by confocal microscopy when compared to normal cells, indicating H/R-induced mitochondria dysfunction in H9c2 cells (FIGS. 14A and 14B). However, the decrease in Rh123 fluorescence upon exposure with H/R was restored by AP1 (FIGS. 14C and 14D).

Figure 15:
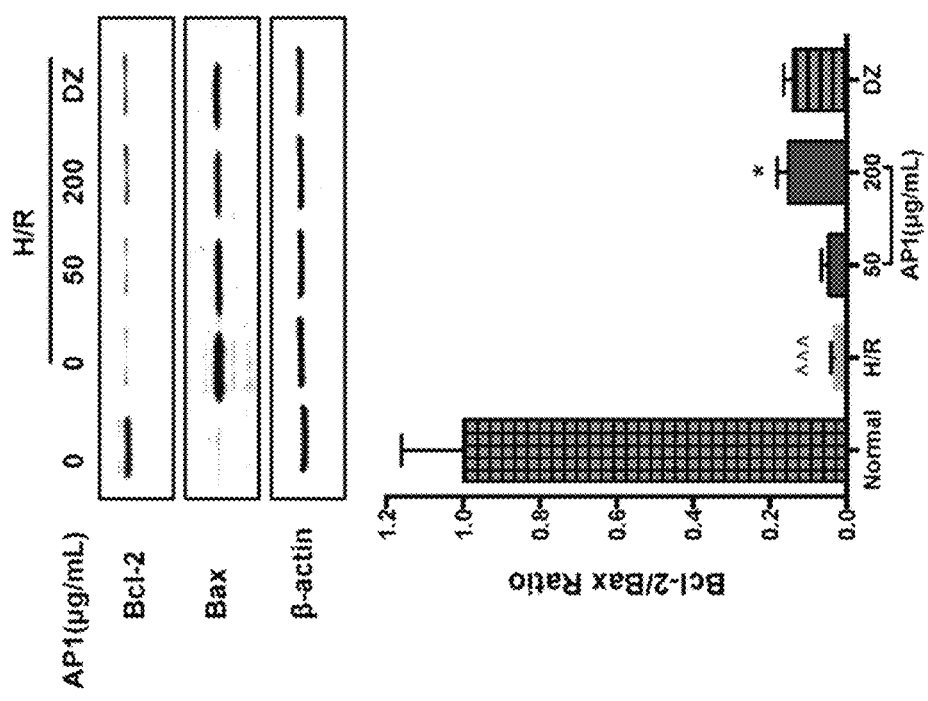
FIG. 15 illustrates the effects of the carbohydrate composition AP1 on Bcl-2 and Bax protein expression with Western blotting analysis. H9c2 cells were pretreated without (H/R) or with various concentrations of AP1 (50 µg/mL and 200 µg/mL) or positive control (DZ, 100 µM) for 1 h, and then exposed to hypoxia for 3 h followed by reoxygenation for another 4 h. The normal group (Normal) was always maintained in normoxic condition. The cells were collected for Western blotting analysis. The blot was probed with antibodies specific to Bcl-2 and Bax and read by densitometric analysis. Normalization of Western blot was ensured by β-actin. Identical results were obtained in three independent experiments. All values are expressed as mean±SD. $^{\wedge\wedge\wedge}$P<0.001 vs. Normal, *P<0.05 vs. H/R. The figure demonstrates H/R reduced the Bcl-2/Bax ratio, but AP1 increased the Bcl-2/Bax ratio.

The balance of anti- and pro-apoptotic proteins in the Bcl-2 family plays an important role in the control of mPTP opening and cell survival against ischemia-reperfusion injuries (Chen, Q. et al., PLoS One 10, e0118834, 2015). To determine whether H/R induced cell apoptosis is associated with a change in the Bcl-2 family proteins, the expression of anti-apoptotic (Bcl-2) and pro-apoptotic (Bax) proteins was determined by Western blot analysis. An increase in the expression of the pro-apoptotic Bax and a decrease in the expression of the anti-apoptotic Bcl-2 were found after H9c2 cells were treated with H/R. However, pretreatment with AP1 antagonized all the above effects induced by H/R treatment and significantly attenuated the decrease of the intracellular ratio of Bcl-2 to Bax (FIG. 15).

Figure 16:
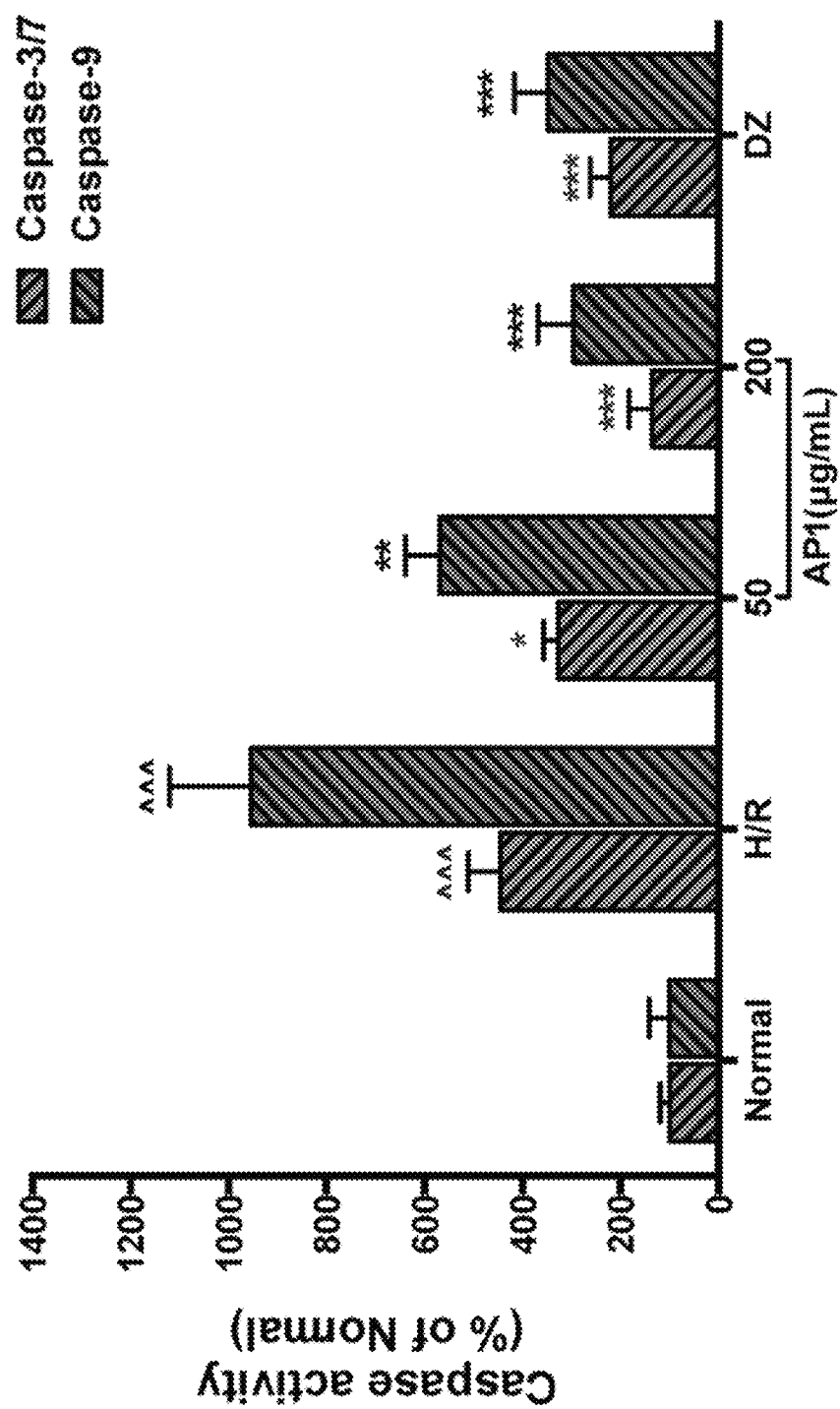
FIG. 16 illustrates the effects of the carbohydrate composition AP1 on activities of caspase-3/7 and -9 induced by H/R injury in H9c2 cells. H9c2 cells were pretreated without (H/R) or with various concentrations of AP1 (50 µg/mL and 200 µg/mL) or positive control (DZ, 100 µM) for 1 h, and then exposed to hypoxia for 3 h followed by reoxygenation for another 4 h. The normal group (Normal) was always maintained in normoxic condition. The activities of caspase-3/7 and -9 were determined using a Caspase-Glo assay kit. Identical results were obtained in three independent experiments. All values are expressed as mean±SD. $^{\wedge\wedge\wedge}$P<0.001 vs. Normal, *P<0.05 vs. H/R, P<0.01 vs. H/R, *P<0.001 vs. H/R.

An additional test was performed to assess myocardial apoptosis with greater specificity. To investigate whether the blocking H/R induced apoptosis by AP1 is dependent on caspase activation, the activities of caspase-3/7 and -9 have been examined, which are initiating caspases in mitochondria-mediated apoptosis pathway. As shown in FIG. 16, after treatment of cells with H/R, the activities of caspase-3/7, -9 were enhanced by 4.5 and 9.6-fold, as compared to normal group. However, pretreatment with AP1 (50 and 200 μg/mL) significantly attenuated these increase of caspase activities in a dose-dependent manner.

Figure 17:
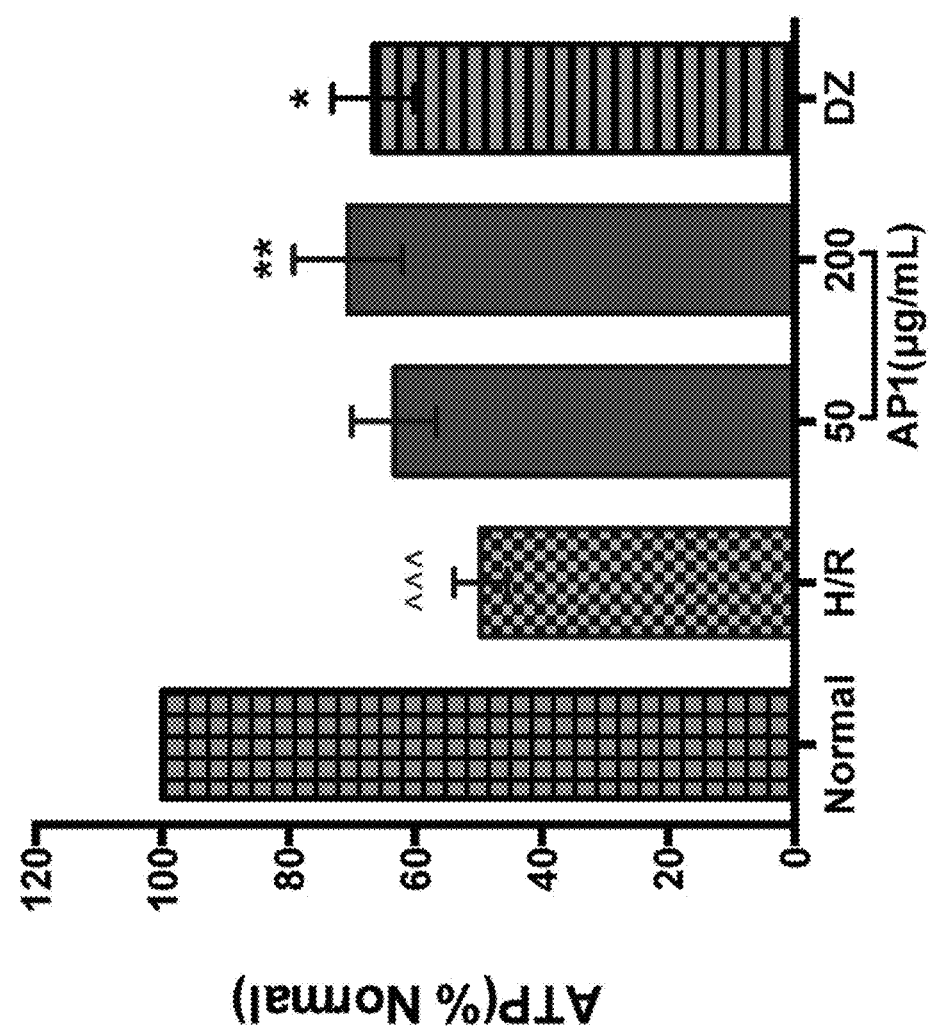
FIG. 17 illustrates the effects of the carbohydrate composition AP1 on ATP levels. H9c2 cells were pretreated without (H/R) or with various concentrations of AP1 (50 µg/mL and 200 µg/mL) or positive control (DZ, 100 µM) for 1 h, and then exposed to hypoxia for 3 h followed by reoxygenation for another 4 h. The normal group (Normal) was always maintained in normoxic condition. The ATP level was measured by a luminescent ATP detection assay kit. Identical results were obtained in three independent experiments. All values are expressed as mean±SD. $^{\wedge\wedge\wedge}$P<0.001 vs. Normal, *P<0.05 vs. H/R, **P<0.01 vs. H/R.

ATP generation is also an essential marker for mitochondrial function (Dong, G. et al. Mitochondrion 26, 7-18, 2016). ATP levels of H/R group were significantly lower than that of the normal group, which was alleviated more by 200 μg/mL AP1 treatment (FIG. 17). These results suggested that AP1 supplementation largely preserved mitochondrial function under H/R conditions in cardiac cells.

Figure 18A:
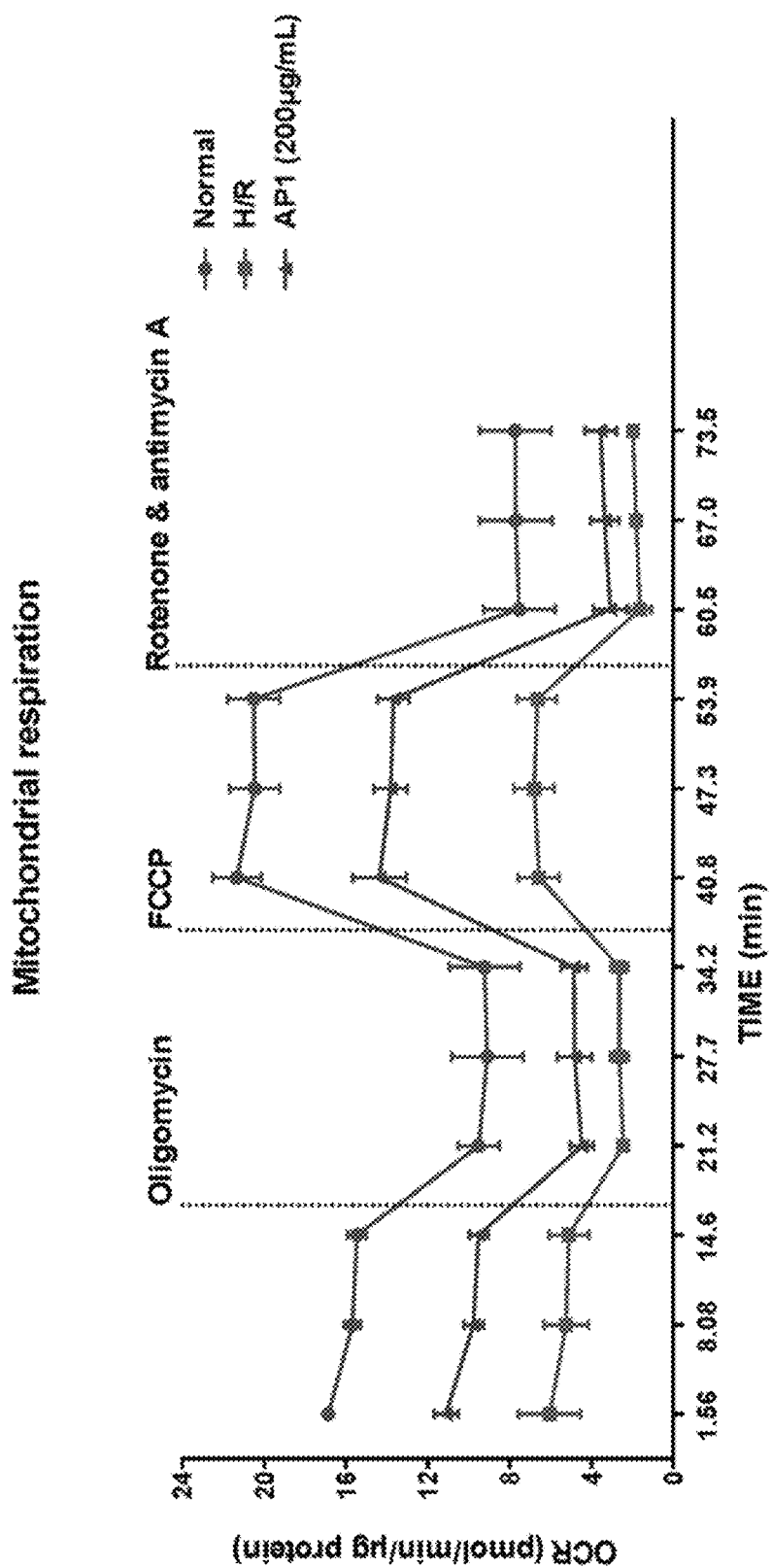
FIGS. 18A and 18B show the effects of the carbohydrate composition AP1 on the oxygen consumption rate (OCR) (FIG. 18A) and its linked parameters of mitochondrial respiration (FIG. 18B). The cells were pretreated without or with AP1 (200 µg/mL) for 1 h, and then exposed to hypoxia for 3 h followed by reoxygenation for another 4 h. The normal group (Normal) was always maintained in normoxic condition. OCR was measured in the presence of successive injections of oligomycin (10 µM), FCCP (2.0 µM), and Rotenone &antimycin A (0.5 µM) using the XFp extracelluar Flux Analyzer. The OCR at basal respiration, maximal respiration, proton leak and ATP production were calculated. Identical results were obtained in three independent experiments. All values are expressed as mean±SD. $^{\wedge\wedge}$P<0.01 vs. Normal, *P<0.05 vs. H/R.
Figure 18B:
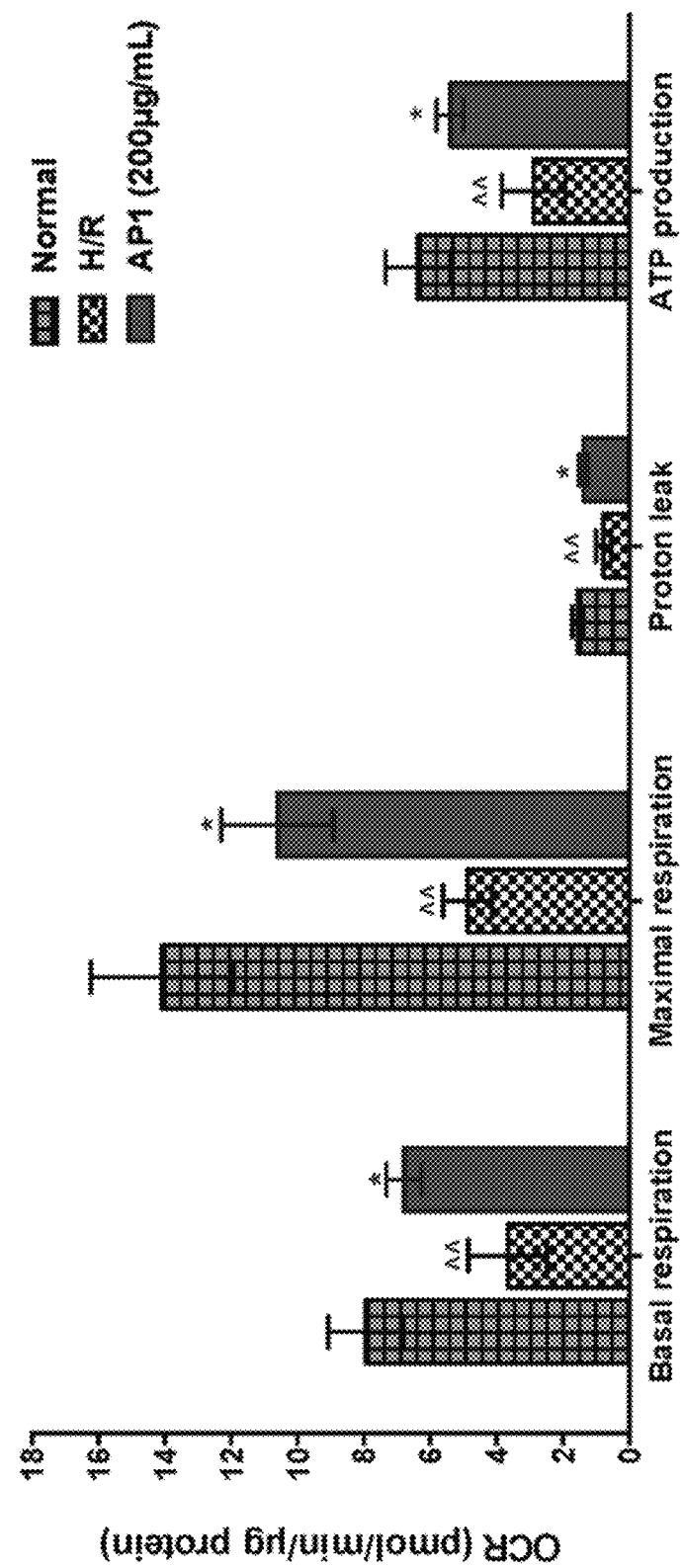

OCR is an important feature of mitochondrial function. Compared with the normal cells, H/R significantly decreased OCR (Basal) and OCR (Maximal), indicating that H/R inhibits oxygen consumption. With AP1 treatment, OCR (Maximal) was significantly increased, indicating that AP1 ameliorated the oxygen consumption in H/R. (FIG. 18). All these indicate that the carbohydrate composition AP1 protects the mitochondrial function against H/R injury by increasing the MMP, ATP content, and mitochondrial respiration, and by increasing Bcl-2/Bax ratio.

The invention claimed is:

1. A method of treating a subject suffering from an ischemic condition comprising administering an effective amount of a carbohydrate composition extracted from *Panax ginseng* to the subject; wherein the carbohydrate composition comprises a carbohydrate portion with a content of more than 80% by weight based on the weight of the carbohydrate composition and wherein the carbohydrate portion comprises at least 50% by weight of glucose and at least 5% by weight of galactose based on the weight of the carbohydrate portion.

2. The method of claim 1, wherein the ischemic condition is ischemic heart disease.

3. The method of claim 1, wherein the carbohydrate composition comprises at least one polysaccharide which is an acidic heteroglycan.

4. The method of claim 1, wherein the carbohydrate composition comprises a carbohydrate portion with a content of more than 85% by weight based on the weight of the carbohydrate composition.

5. The method of claim 1, wherein the carbohydrate composition comprises a carbohydrate portion with a content of more than 85% by weight based on the weight of the carbohydrate composition and wherein the carbohydrate portion comprises 70% to 80% by weight of glucose, 8% to 18% by weight of galactose, 0.5% to 10% by weight of galacturonic acid, 0.1% to 8% by weight of arabinose and 0.1% to 5% by weight of glucuronic acid based on the weight of the carbohydrate portion.

6. The method of claim 1, wherein the carbohydrate composition is extracted from *Panax ginseng* with an extraction comprising steps of:
   (i) providing a crude *Panax ginseng* extract comprising contacting *Panax ginseng* plant material with an extraction solvent comprising an aliphatic alcohol;
   (ii) isolating the carbohydrate composition from the crude *Panax ginseng* extract of step (i).

7. The method of claim 6, wherein step (i) comprises steps of:
   a) contacting the *Panax ginseng* plant material with the extraction solvent for obtaining a mixture of *Panax ginseng* plant material and extraction solvent, wherein the extraction solvent comprises ethanol;
   b) subjecting the mixture of step a) to one or more of stirring, shaking, heating, sonication and/or allowing the mixture of step a) to stand at a temperature of between 20° C. and 30° C.;
   c) isolating the crude *Panax ginseng* extract by filtering the mixture after step b), concentrating the filtrate under vacuum and drying the concentrated filtrate.

8. The method of claim 6, wherein step (ii) comprises steps of:
   a) optionally fractionating the crude *Panax ginseng* extract for obtaining a carbohydrate-enriched *Panax ginseng* extract;
   b) adding water and an aliphatic alcohol to the crude *Panax ginseng* extract of step (i) or to the carbohydrate-enriched *Panax ginseng* extract of step a) for obtaining a carbohydrate-enriched precipitate;
   c) subjecting the carbohydrate-enriched precipitate to an anion-exchange chromatography with an eluting solvent for obtaining an eluate with the carbohydrate composition;
   d) concentrating the eluate of step c) comprising at least partially removing the eluting solvent for obtaining a residue, dialyzing the residue and freeze-drying.

9. The method of claim 8, wherein the aliphatic alcohol in step b) is ethanol and wherein the crude *Panax ginseng* extract of step (i) or the carbohydrate-enriched *Panax ginseng* extract of step a) is mixed with water before adding ethanol such that an ethanol concentration of about 70 Vol.-% is obtained.

10. The method of claim 8, wherein fractionating the crude *Panax ginseng* extract in step a) comprises subjecting the crude *Panax ginseng* extract to fluid-fluid chromatography, and wherein the fluid-fluid chromatography is carried out as high-speed counter-current chromatography with a two-phase solvent system comprising at least two of an aliphatic alcohol, water and an ester.

11. The method of claim 8, wherein the anion-exchange chromatography in step c) is carried out with an anion exchange resin comprising diethylamino ethyl groups and wherein the eluting solvent comprises water and sodium chloride.

12. A method of reducing the risk of an ischemia-reperfusion injury in a subject suffering from an ischemic condition comprising administering an effective amount of a carbohydrate composition extracted from *Panax ginseng* to the subject; wherein the carbohydrate composition comprises a carbohydrate portion with a content of more than 80% by weight based on the weight of the carbohydrate composition and wherein the carbohydrate portion comprises at least 50% by weight of glucose and at least 5% by weight of galactose based on the weight of the carbohydrate portion.

13. The method of claim 12, wherein the carbohydrate composition comprises at least one polysaccharide which is an acidic heteroglycan.

14. The method of claim 12, wherein the carbohydrate composition comprises a carbohydrate portion with a content of more than 85% by weight based on the weight of the carbohydrate composition and wherein the carbohydrate portion comprises 70% to 80% by weight of glucose, 8% to 18% by weight of galactose, 0.5% to 10% by weight of galacturonic acid, 0.1% to 8% by weight of arabinose and 0.1% to 5% by weight of glucuronic acid based on the weight of the carbohydrate portion.

15. A method of protecting cells against hypoxia and reoxygenation induced cell death comprising contacting the cells with a carbohydrate composition extracted from *Panax ginseng*; wherein the carbohydrate composition comprises a carbohydrate portion with a content of more than 80% by weight based on the weight of the carbohydrate composition and wherein the carbohydrate portion comprises at least 50% by weight of glucose and at least 5% by weight of galactose based on the weight of the carbohydrate portion.

16. The method of claim 15, wherein the cells are cardiomyocytes.

17. The method of claim 15, wherein the cells are contacted with the carbohydrate composition in a concentration of between 6.25 µg/ml and 800 µg/ml for at least 12 h.

18. The method of claim 15, wherein the carbohydrate composition comprises a carbohydrate portion with a content of more than 85% by weight based on the weight of the carbohydrate composition and wherein the carbohydrate portion comprises 70% to 80% by weight of glucose, 8% to 18% by weight of galactose, 0.5% to 10% by weight of galacturonic acid, 0.1% to 8% by weight of arabinose and 0.1% to 5% by weight of glucuronic acid based on the weight of the carbohydrate portion.

* * * * *